(12) United States Patent
Greenberg et al.

(10) Patent No.: US 11,399,788 B2
(45) Date of Patent: Aug. 2, 2022

(54) SYSTEMS AND METHODS FOR TISSUE DISCRIMINATION VIA MULTI-MODALITY CODED APERTURE X-RAY IMAGING

(71) Applicant: Duke University, Durham, NC (US)

(72) Inventors: Joel Alter Greenberg, Durham, NC (US); Anuj J. Kapadia, Durham, NC (US)

(73) Assignee: Duke University, Durham, NC (US)

( * ) Notice: Subject to any disclaimer, the term of this patent is extended or adjusted under 35 U.S.C. 154(b) by 135 days.

(21) Appl. No.: 16/743,718

(22) Filed: Jan. 15, 2020

(65) Prior Publication Data
US 2020/0225371 A1     Jul. 16, 2020

Related U.S. Application Data

(60) Provisional application No. 62/792,849, filed on Jan. 15, 2019.

(51) Int. Cl.
*A61B 6/00*     (2006.01)
*G01T 1/29*     (2006.01)
(Continued)

(52) U.S. Cl.
CPC .............. *A61B 6/483* (2013.01); *A61B 6/06* (2013.01); *A61B 6/40* (2013.01); *A61B 6/405* (2013.01); *A61B 6/4035* (2013.01); *A61B 6/4208* (2013.01); *A61B 6/4233* (2013.01); *A61B 6/4291* (2013.01); *A61B 6/5205* (2013.01); *A61B 6/54* (2013.01); *A61B 6/542* (2013.01);
(Continued)

(58) Field of Classification Search
CPC ........... A61B 6/06; A61B 6/40; A61B 6/4035; A61B 6/405; A61B 6/42; A61B 6/4208; A61B 6/4233; A61B 6/4291; A61B 6/483; A61B 6/52; A61B 6/5205; A61B 6/54; A61B 6/542; A61B 6/545; A61B 6/032; A61B 6/035; A61B 6/544
USPC .............. 378/2, 16, 19, 62, 86–90, 147, 149
See application file for complete search history.

(56) References Cited

U.S. PATENT DOCUMENTS 4,228,420 A * 10/1980 Fenimore ................ G01T 1/295
                                                                378/2
4,677,681 A * 6/1987 Klausz ................... A61B 6/025
                                                             250/363.07
(Continued)

FOREIGN PATENT DOCUMENTS

| EP | 2021784 A2 | 2/2009 |
|---|---|---|
| EP | 3182104 A2 | 6/2017 |

(Continued)

OTHER PUBLICATIONS

Ashton, J. R., et al. "Dual-energy micro-CT functional imaging of primary lung cancer in mice using gold and iodine nanoparticle contrast agents: a validation study." PloS one 9.2 (2014).
(Continued)

*Primary Examiner* — Allen C. Ho
(74) *Attorney, Agent, or Firm* — Quarles & Brady, LLP

(57) ABSTRACT

Systems and methods for tissue discrimination are disclosed. The systems and the methods utilize coded x-ray beams. Transmission signals and scatter signals are utilized to determine tissue properties.

20 Claims, 16 Drawing Sheets
(14 of 16 Drawing Sheet(s) Filed in Color)

(51) Int. Cl.
  *G01T 1/161* (2006.01)
  *A61B 6/06* (2006.01)
  *G02B 27/30* (2006.01)

(52) U.S. Cl.
  CPC ............ *A61B 6/545* (2013.01); *G01T 1/1615* (2013.01); *G01T 1/295* (2013.01); *A61B 6/50* (2013.01); *A61B 6/547* (2013.01); *G02B 27/30* (2013.01)

(56) References Cited

U.S. PATENT DOCUMENTS

| | | | | |
|---|---|---|---|---|
| 5,717,733 | A * | 2/1998 | Kurbatov | G01N 23/207 378/2 |
| 5,745,543 | A | 4/1998 | De Bokx | |
| 6,737,652 | B2 * | 5/2004 | Lanza | G01T 1/295 250/237 R |
| 6,950,495 | B2 | 9/2005 | Nelson | G01N 23/203 378/156 |
| 7,463,712 | B2 * | 12/2008 | Zhu | A61B 6/5282 378/2 |
| 7,476,863 | B2 * | 1/2009 | Lamadie | G01T 1/295 250/237 R |
| 7,551,709 | B2 | 6/2009 | Schlomka | |
| 7,580,499 | B2 | 8/2009 | Van Stevendaal | |
| 7,623,614 | B2 * | 11/2009 | Shefsky | G01N 23/02 378/2 |
| 7,646,850 | B2 | 1/2010 | MacDonald | |
| 7,809,109 | B2 * | 10/2010 | Mastronardi | G01N 23/20083 378/90 |
| 7,835,495 | B2 | 11/2010 | Harding | |
| 7,850,499 | B2 | 12/2010 | Uno | |
| 8,194,821 | B2 * | 6/2012 | Seppi | G21K 1/10 378/62 |
| 8,462,913 | B2 | 6/2013 | Evans | |
| 8,503,602 | B2 | 8/2013 | Lafferty | |
| 8,989,342 | B2 * | 3/2015 | Liesenfelt | G01N 23/203 378/12 |
| 9,335,281 | B2 | 5/2016 | Marks | |
| 9,719,947 | B2 * | 8/2017 | Yun | G01N 23/20075 |
| 9,820,709 | B2 * | 11/2017 | Melman | A61B 6/542 |
| 9,921,173 | B2 * | 3/2018 | Evans | G01N 23/046 |
| 9,931,087 | B2 * | 4/2018 | Melman | A61B 6/4233 |
| 9,952,163 | B2 * | 4/2018 | Endrizzi | A61B 6/484 |
| 10,004,464 | B2 * | 6/2018 | Brady | A61B 6/032 |
| 10,327,717 | B2 * | 6/2019 | Melman | A61B 6/4225 |
| 10,859,517 | B2 * | 12/2020 | Hesselink | G01N 23/041 |
| 10,869,641 | B2 * | 12/2020 | Ergler | G21K 1/025 |
| 2008/0118027 | A1 | 5/2008 | Gaved | |
| 2008/0139914 | A1 | 6/2008 | Gaved | |
| 2015/0362443 | A1 | 12/2015 | Evans | |

FOREIGN PATENT DOCUMENTS

| | | |
|---|---|---|
| WO | 2014111684 A1 | 7/2014 |
| WO | 2015023741 A1 | 2/2015 |

OTHER PUBLICATIONS

Batchelar, D. L., et al. "Bone-composition imaging using coherent-scatter computed tomography: Assessing bone health beyond bone mineral density." Medical Physics 33(4), 904-915 (2006).

Brisson, B. K., et al. "Type III collagen directs stromal organization and limits metastasis in a murine model of breast cancer." The American journal of pathology 185.5 (2015): 1471-1486.

Castro, C. R. F., et al. "Coherent scattering characteristics of normal and pathological breast human tissues." Radiation Physics and chemistry 71 (2004): 649-651.

Delfs, J., et al. "Energy-dispersive coherent scatter computed tomography." Applied physics letters 88.24 (2006): 243506.

Desouky, O. S., et al. "X-ray scattering signatures of ß-thalassemia." Nuclear Instruments and Methods in Physics Research Section A: Accelerators, Spectrometers, Detectors and Associated Equipment 607.2 (2009): 463-469.

Dicken, A., et al. "Combined X-ray diffraction and kinetic depth effect imaging." Optics express 19.7 (2011): 6406-6413.

Elshemey, W. M., et al. "The diagnostic capability of x-ray scattering parameters for the characterization of breast cancer." Medical physics 37.8 (2010): 4257-4265.

Greenberg, J. A. et al. "Coding and sampling for compressive x-ray diffraction tomography," Proc. SPIE 8858, 885813-885813-11 (2013).

Greenberg, J. A. et al. "Snapshot molecular imaging using coded energy-sensitive detection," Opt. Express 21, 25480-25491 (2013).

Greenberg, J. A. et al. Optimization of a coded aperture coherent scatter spectral imaging system for medical imaging, 2015. Proceedings vol. 9412, Medical Imaging 2015: Physics of Medical Imaging; 94125E (2015); doi:10.1117/12.2082110.

Greenberg, J. A. et al. Structured illumination for tomographic X-ray diffraction imaging . Analyst, 709-713, doi:10.1039/C3AN01641B (2014).

Griffiths, J. et al. Angular dispersive diffraction microCT of small breast tissue samples. Radiation Physics and Chemistry 77, 373-380 (2008).

Grin, A., et al. "Measuring extent of ductal carcinoma in situ in breast excision specimens: a comparison of 4 methods." Archives of pathology & laboratory medicine 133.1 (2009): 31-37.

Harding, G. Effective density and atomic number determined from diffraction profiles. Proc. SPIE 6319, Hard X-Ray and Gamma-Ray Detector Physics and Penetrating Radiation Systems VIII, (63191O):63191O-63191O-9, 2006.

Harding, G. et al, "Coherent x-ray scatter imaging and its applications in biomedical science and industry," Radiation Physics and Chemistry 56(12), 229-245 (1999).

Harding, G. et al. Elastic scatter computed tomography. Phys Med Biol 30, 183-186 (1985).

Harding, G. et al. Energy-dispersive x-ray diffraction tomography. Physics in Medicine and Biology, 35(1):33, 1990.

Harding, G. et al. Status and outlook of coherent-x-ray scatter imaging. J. Opt. Soc. Am. A, 4(5):933-944, May 1987.

Harding, G. et al. X-ray diffraction computed tomography. Med Phys 14, 515-525 (1987).

Hogan, J. P., et al. "Fluorescent computer tomography: a model for correction of X-ray absorption." IEEE Transactions on Nuclear Science 38.6 (1991): 1721-1727.

Huo, L. A practical approach to grossing breast specimens. Annals of Diagnostic Pathology 15, 291-301, doi:10.1016/i.anndiagpath.2011.03.005.

Jacques, SDM et al. A laboratory system for element specific hyper-spectral x-ray imaging. Analyst, 138:755-759, 2013.

Kidane, G., et al. X-ray scatter signatures for normal and neoplastic breast tissues. Phys Med Biol 44, 1791-1802 (1999).

King, BW, et al, "Measurement of coherent scattering form factors using an image plate," Physics in Medicine and Biology 54(20), 6437 (2009). With Corrigendum.

King, BW, et al, "X-ray coherent scattering form factors of tissues, water and plastics using energy dispersion," Physics in Medicine and Biology 56(14), 4377 (2011).

Lakshmanan, M.N. et al, "Experimental implementation of coded aperture coherent scatter spectral imaging of cancerous and healthy breast tissue samples," Proc. SPIE 9412, 94121F-94121F-6 (2015).

Lakshmanan, M.N. et al, "Volumetric x-ray coherent scatter imaging of cancer in resected breast tissue: a Monte Carlo study using virtual anthropomorphic phantoms," Phys. Med. Biol. 60(16), 6355-6370 (2015).

Lakshmanan, M.N. et al. "Design and implementation of coded aperture coherent scatter spectral imaging of cancerous and healthy breast tissue samples." Journal of Medical Imaging 3.1 (2016): 013505.

Lakshmanan, M.N. et al. Accuracy assessment and characterization of x-ray coded aperture coherent scatter spectral imaging for breast cancer classification. Journal of Medical Imaging, 4(1):013505, 2017.

Lakshmanan, M.N. et al. Coded aperture coherent scatter imaging for breast cancer detection: a monte carlo evaluation, 2016. Proc.

(56) References Cited

OTHER PUBLICATIONS

SPIE 9783, Medical Imaging 2016: Physics of Medical Imaging, 978321 (Mar. 22, 2016); doi:10.1117/12.2216482.
Landheer K. et al. Synchrotron-based coherent scatter x-ray projection imaging using an array of monoenergetic pencil beams. Review of Scientific Instruments, 83(9):095114, 2012.
Lazzari, O. et al, "Reconstructive colour x-ray diffraction imaging—a novel teddi imaging method," Analyst 134, 1802-1807(2009).
Leclair, R. J., et al. Model predictions for the wide-angle x-ray scatter signals of healthy and malignant breast duct biopsies. Journal of medical imaging 2, 043502-043502, doi:10.1117/1.JMI.2.4.043502 (2015).
Maccabe, K. et al. Pencil beam coded aperture x-ray scatter imaging. Opt Express 20, 16310-16320 doi:http://dx.doi.org/10.1364/OE.20.016310 (2012).
Morris, R. E., et al. "Validation of coded aperture coherent scatter spectral imaging for normal and neoplastic breast tissues via surgical pathology." Medical Imaging 2016: Physics of Medical Imaging. vol. 9783. International Society for Optics and Photonics, 2016.
Odinaka, I., et al. "Coded aperture x-ray diffraction imaging with transmission computed tomography side-information." Medical Imaging 2016: Physics of Medical Imaging. vol. 9783. International Society for Optics and Photonics, 2016.
O'Flynn, D., et al. Explosive detection using pixellated x-ray diffraction (pixd). Journal of Instrumentation, 8(03):P03007, 2013.
Ryan, E. A., et al. "Breast tissue classification using x-ray scattering measurements and multivariate data analysis." Physics in Medicine & Biology 52.22 (2007): 6679.
Starfield, D. M. et al, "High transparency coded apertures in planar nuclear medicine imaging," in Engineering in Medicine and Biology Society, 2007. EMBS 2007. 29th Annual International Conference of the IEEE, 4468-4471 (2007).
Sun, B. et al. The performance of a fast testing system for illicit materials detection based on energy-dispersive x-ray diffraction technique. Microchemical Journal, 95(2):293-297, 2010.
Theodorakou C. et al. "The classification of secondary colorectal liver cancer in human biopsy samples using angular dispersive x-ray diffraction and multivariate analysis," Physics in Medicine and Biology 54(16), 4945 (2009).
Theodorakou C. et al. Human soft tissue analysis using x-ray or gamma-ray techniques. Physics in Medicine and Biology, 53(11):R111, 2008.
Westmore, M. S., et al. "Angular-dependent coherent scatter measured with a diagnostic x-ray image intensifier-based imaging system." Medical physics 23.5 (1996): 723-733.
Yu, D., et al. "Energy dispersive X-ray diffraction research using coherence function." Procedia Engineering 7 (2010): 165-171.

\* cited by examiner

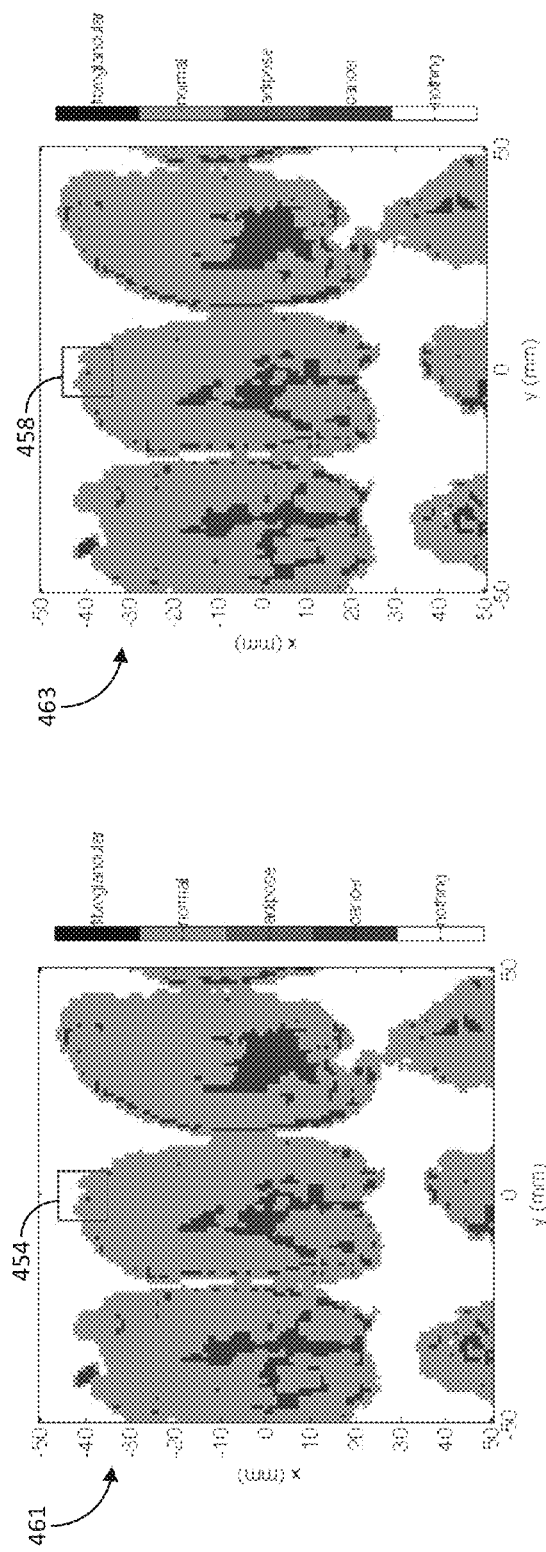
FIG. 14A
FIG. 14B
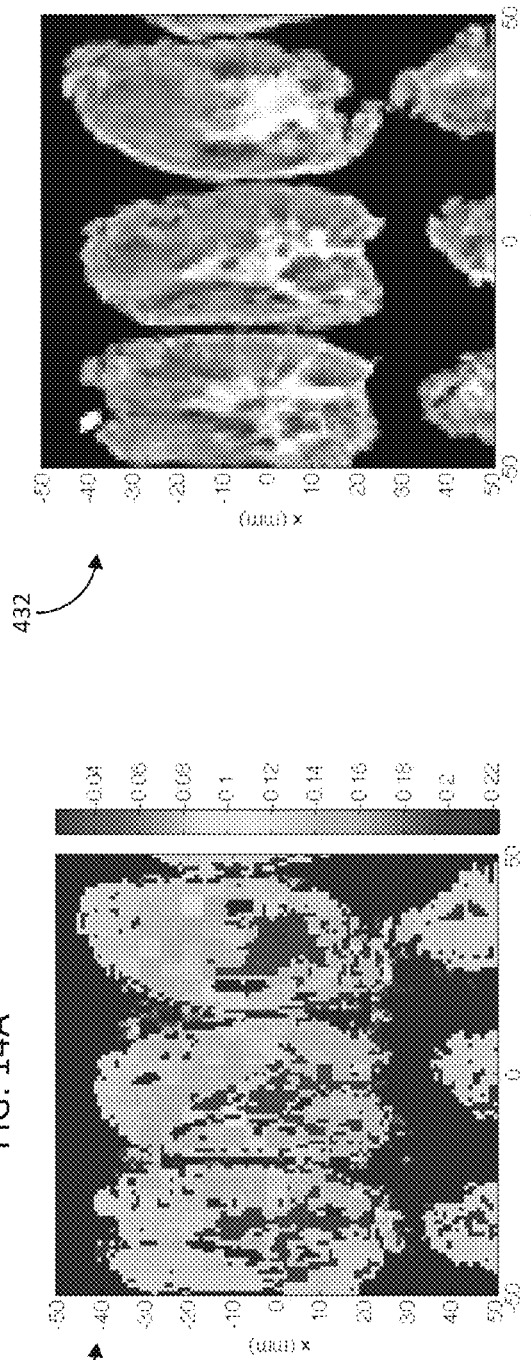
FIG. 14C
FIG. 14D

SYSTEMS AND METHODS FOR TISSUE DISCRIMINATION VIA MULTI-MODALITY CODED APERTURE X-RAY IMAGING

CROSS-REFERENCE TO RELATED APPLICATIONS

The present application claims priority to U.S. Provisional Patent Application Ser. No. 62/792,849 filed Jan. 15, 2019, the disclosure of which is incorporated herein by reference in its entirety.

STATEMENT REGARDING FEDERALLY FUNDED RESEARCH

Not applicable.

BACKGROUND

The first application of X-rays was to perform medical imaging in 1895. Over the last hundred years, X-ray technologies have developed substantially and are ubiquitous and essential in medical, security, and industrial imaging. Much effort has been spent on developing new components, algorithms, and architectures for X-ray imaging, but the bulk of this effort has been confined to transmission imaging (e.g., radiography or computed tomography). However, recent work has demonstrated that measuring the scattered X-rays (i.e., those that interact with the target object and are subsequently deflected) provides additional information that can result in improved system performance. While useful, X-ray scatter imaging has historically suffered from technical challenges related to a combination of high system cost, long acquisition times, and excessive dose.

The literature of transmission imaging in medical imaging is extensive. Several of the most relevant areas include: standard transmission X-ray systems; conventional mammography; breast/lung CT; spectral CT; and systems and methods for rapid stereotactic breast biopsy analysis.

A variety of coherent scatter imaging methods also exist. For some existing x-ray systems, one typically requires an x-ray source, collimators (or coded apertures), and detectors. Depending on the characteristics of these elements and their geometric arrangement, a variety of different design choices emerge, including the use of one or more of the following: polychromatic or monochromatic (or, more generally, filtered vs. not filtered) sources; multiplexed or non-multiplexed measurement schemes; angle dispersive (fixed energy, varying angle) or energy dispersive (fixed angle, varying energy); energy sensitive or energy integrating detectors; snapshot or multi-frame acquisitions; and compressive (dimension-reducing) or non-compressive measurement schemes. Explicit examples of previously-investigated molecular imaging approaches include coherent scatter computed tomography (CSCT), energy dispersive x-ray diffraction tomography (EXDT), kinetic depth effect x-ray diffraction (KDEXRD), and the use of annular beams. While variations on these approaches have resulted in faster imaging with relaxed source constraints, none of these approaches are ideal for fast imaging over an object which is relatively thin but has a large cross-sectional (transverse) area.

Other related work has been done using coded apertures. Examples include coded aperture x-ray scatter imaging (CAXSI), coded aperture coherent scatter spectral imaging (CACSSI), and structured illumination XRD. All of these approaches are focused on imaging thick (many cm in extent) samples of arbitrary materials.

There has been some previous work on combining transmission and scatter imaging using the CSCT architecture. However, this approach uses full CT (rather than radiography), requires rotation of the sample or X-ray source, and does not suggest the possibility of using the same detectors for scatter and transmission imaging.

A variety of studies have considered the use of XRD for tissue analysis previously. However, all have focused on either the use of conventional, non-imaging XRD (i.e., with no spatial resolution), or have focused on the use of CSCT or EXDT (usually requiring either hours of scan time or ultra-bright, expensive sources such as synchrotrons). These studies have demonstrated the utility of such a measurement and provided insight into the underlying biology responsible for the dependence of the XRD form factors on the tissue type, but are not practical in size, weight, scan time, or cost to pathological imaging in a clinical setting.

SUMMARY

In one aspect, the present disclosure provides a system. The system includes an x-ray source, a first coded aperture, a sample mount, a second coded aperture, an x-ray detector array, a processor, and a memory. The x-ray source, in use, produces an x-ray energy. The first coded aperture is positioned to receive the x-ray energy. In use, the first coded aperture produces at least two coded x-ray beams from the x-ray energy. The sample mount has a sample location positioned to allow the at least two coded x-ray beams to pass through the sample location. The sample mount is configured to retain a sample at the sample location. The second coded aperture is positioned to receive the at least two coded x-ray beams. In use, the second coded aperture isolates transmission signals and scatter signals from each of the at least two coded x-ray beams. The x-ray detector array includes a plurality of x-ray detector pixels. The plurality of x-ray detector pixels are positioned to receive the transmission signals and the scatter signals. The processor is in direct or indirect electronic communication with the x-ray source, the first coded aperture, the second coded aperture, and the x-ray detector array. The memory has stored thereon a tissue identification algorithm and instruction. The instruction, when executed by the processor, cause the processor to: direct the x-ray source to emit the x-ray energy; direct the first coded aperture to produce the at least two coded x-ray beams from the x-ray energy; record a relative position of the sample location; direct the second coded aperture and the x-ray detector array to acquire transmission data and diffraction data for each of the at least two coded x-ray beams; determine one or more properties of a tissue sample positioned within the sample location of the sample mount using the tissue identification algorithm and the transmission data and/or the diffraction data; and generate a report including the relative position of the sample location and the one or more properties of the tissue sample.

In another aspect, the present disclosure provides a method. The method includes the following steps: a) transmitting at least two coded x-ray beams from a coded x-ray source into a sample; b) receiving transmission signals corresponding to each of the at least two coded x-ray beams; c) receiving scatter signals corresponding to each of the at least two coded x-ray beams; d) determining, using a computer-executed tissue identification algorithm, one or more tissue properties based on the transmission signals and/or the scatter signals; and e) generate a report including the one or more tissue properties.

BRIEF DESCRIPTIONS OF THE DRAWINGS

The patent or application file contains at least one drawing executed in color. Copies of this patent or patent application publication with color drawing(s) will be provided by the office upon request and payment of the necessary fee.

FIG. 14A is a plot of reconstructed data, in accordance with the present disclosure.

FIG. 14B is a plot of ground truth data corresponding to the reconstructed data of FIG. 14A, in accordance with the present disclosure.

FIG. 14C is a plot of reconstructed cancer score data, in accordance with the present disclosure.

FIG. 14D is a plot of ground truth transmission data corresponding to the reconstructed cancer score data of FIG. 14C, in accordance with the present disclosure.

Figure 1A:
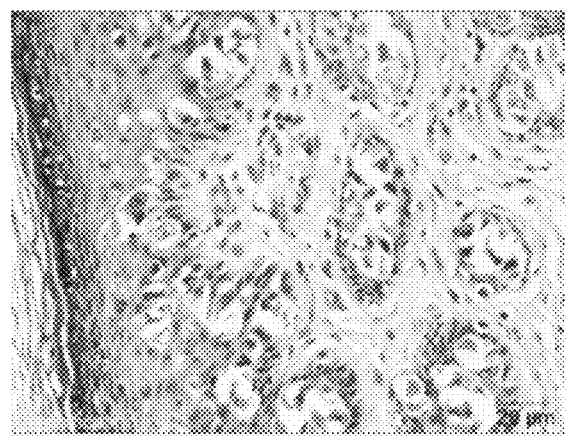
FIG. 1A is a prior art image of a histology slide corresponding to a tissue sample.

Throughout the Figures, the same reference numerals and characters, unless otherwise stated, are used to denote like features, elements, components, or portions of the illustrated embodiments. Moreover, while the present disclosure will now be described in detail with reference to the Figures, it is done so in connection with the illustrative embodiments and is not limited by the particular embodiments illustrated in the Figures.

DETAILED DESCRIPTION

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices, and methods relating to x-ray imaging are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

As used herein, the term "x-ray beam" refers to x-rays propagating along a given vector direction. A pencil x-ray beam is a single x-ray beam. A cone x-ray beam is a plurality of x-ray beams. A fan x-ray beam is a plurality of x-ray beams. In order to achieve two or more x-ray beams using pencil beams, two or more pencil x-ray beams would be required. On the other hand, a single cone x-ray beam and a single fan x-ray beam each contains two or more x-ray beams as defined herein.

As used herein, the term "diameter" refers to a single dimension of an x-ray beam or a plurality of x-ray beams. In the context of a pencil x-ray beam, the diameter is a physical dimension of the pencil x-ray beam that is perpendicular to the direction of x-ray propagation. In the context of a cone x-ray beam, the diameter is a physical dimension of the narrowest part of the beam, which in some cases is defined by an aperture. In the context of a fan x-ray beam, the diameter is a physical dimension of the fan x-ray beam that is perpendicular to the direction of x-ray propagation for all parts of the fan. In other words, the diameter of a fan x-ray beam is the width of the fan.

As used herein, the term "fan angle" refers to the angle defined by the outer portions of a cone x-ray beam or a fan x-ray beam. Typically, the fan angle of the cone x-ray beam is symmetrical in a similar fashion to the geometric shape of a cone. Typically, the fan angle of the fan x-ray beam is defined in a single plane (i.e., the plane in which the fan lies). Suitable fan angles for use in the present disclosure include, but are not limited to, a fan angle of between 1° and 150°, between 5° and 135°, between 10° and 100°, between 15° and 90°, between 45° and 75°, between 60° and 140°, between 90° and 145°, and all other combinations of the lower and upper bounds of these ranges.

As used herein, the term "monochromatic" refers to a spectrum with a width of between 0 keV and 1 keV.

As used herein, the term "narrowband" refers to a spectrum with a width of between 1 keV and 20 keV.

As used herein, the term "broadband" refers to a spectrum with a width of 20 keV or higher.

The various aspects may be described herein in terms of various functional components and processing steps. It should be appreciated that such components and steps may be realized by any number of hardware components configured to perform the specified functions.

In contrast to some of the approaches discussed in the background above, for the application of ex-vivo tissue imaging, it is approximately known what the range of tissue types is and that the thickness will not generally exceed a few centimeters. This allows changing of the measurement approach to allow for fast, efficient imaging across a large area. In addition, the optional inclusion of the use of collimation at the detector to improve the SNR, was not previously considered.

It is worth noting that coherent scatter can also yield effective density and atomic number, Z, of the object if one can measure f(q) in an absolute sense (i.e., if one can measure the absolute scattering cross section of the object, in addition to the location and amplitudes of the relative coherent scatter peaks). Measuring these additional object properties can greatly enhance one's ability to identify a particular material. Unfortunately, because energy-dependent attenuation from all objects along the primary and scattered beams' paths affect the measured value of the cross section, one must obtain a reasonable estimate of the object's attenuation properties [$\mu(r;E)$] in order to correctly obtain f(q). Thus, it is important to measure also the transmitted x-ray signal at each primary beam location. Furthermore, the morphological information contained in the transmission image combined with the potential for dual/multi-energy coarse material information provided therein can greatly add the ability to identify tissue types compared to using either transmission or scatter alone.

Figure 1B:
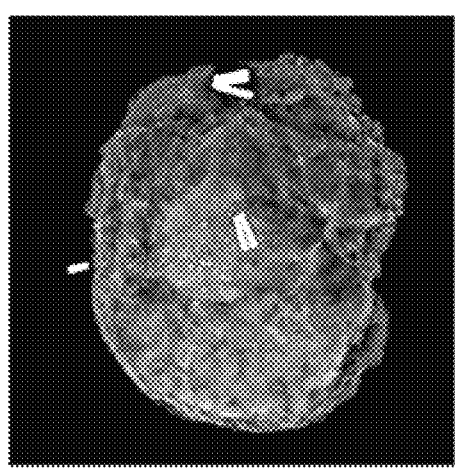
FIG. 1B is a prior art image of a tissue sample.

Referring to FIGS. 1A-1B, existing methods of cancer diagnosis are shown. FIG. 1A shows a histology slide, as an example. Generally, microscopic histological analysis of cellular morphology (i.e., by a trained pathologist) is considered the "gold standard" for cancer diagnosis. However, microscopy has a limited field of view, which limits pathological analysis to less than 10% of the available tissue sample. Accordingly, cancer can be missed or misdiagnosed. Further, analysis of the tissue sample via microscopy is time-intensive, resulting in a low pathology throughput.

FIG. 1B illustrates another existing method of cancer diagnosis. FIG. 1B shows a transmission image of a tissue sample, which includes markers for potential cancerous areas. The transmission image is produced via x-ray systems which, although part of current clinical workflow, fail to actually identify or indicate potential regions of cancer. As shown in FIG. 1B, a skilled physician must review the transmission image and subjectively decide areas to mark for further analysis. The present disclosure addresses the above-mentioned short-comings of existing diagnostic methods, among other things.

Systems

Figure 2:
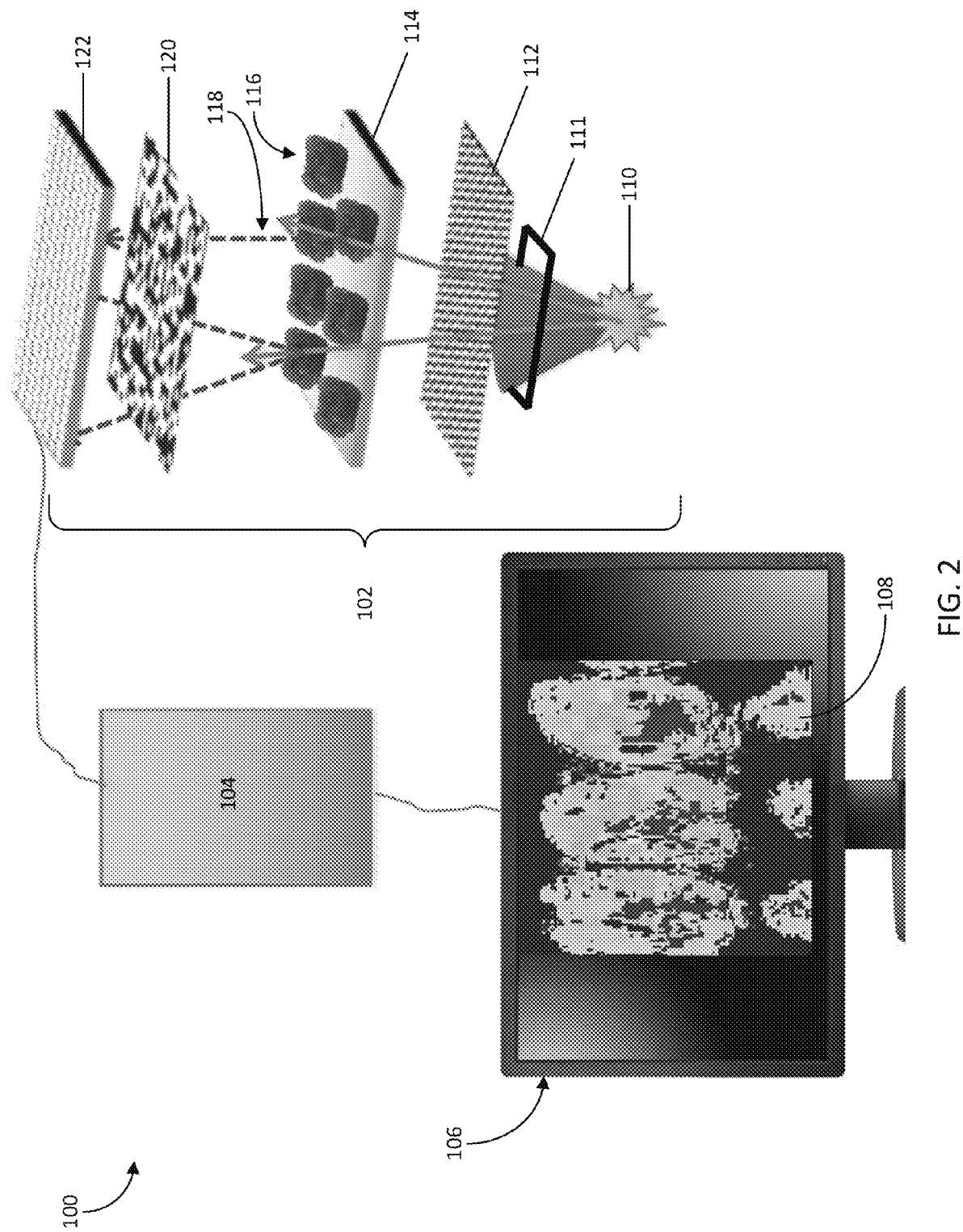
FIG. 2 is a diagram of a system in accordance with aspects of the present disclosure.

This disclosure provides a system. FIG. 2 is a system 100 having an x-ray system 102 in accordance with aspects of the present disclosure. As shown, the system 100 can include an x-ray source 110 (or multiple), a first coded aperture 112, a sample mount 114, a second coded aperture 120, an x-ray detector array 122, and a processor 104 having a memory. Tissue samples 116 may be disposed on the sample mount 114 when the system 100 is in-use. In some implementations, the system 100 can include a display 106 in communication with the processor 104. The display 106 can provide a user interface 108, which can be configured to accept user inputs as well as display outputs of the system 100 (e.g., reports, images, diagnostic data).

The features of the methods described elsewhere herein are applicable to the systems described herein, unless otherwise expressly indicated.

In use, the x-ray source 110 produces an x-ray energy. In some cases, the x-ray source 110 is a broadband x-ray source. In some cases, the x-ray source 110 is a narrowband x-ray source. In some cases, the x-ray source 110 is an x-ray tube. The x-ray source 110 can be configured for operation at between 15 kVp and 150 kVp. The x-ray energy can have an energy of between 1 keV and 150 keV, including but not limited to between 15 keV and 130 keV, between 1 keV and 130 keV, and between 15 keV and 150 keV. The x-ray energy can be configured to provide radiation flux understood by those having ordinary skill in the art to be suitable for a given purpose, including but not limited to a radiation flux of up to 500 mAs. Suitable commercially available x-ray sources 110 include Varian model G1593BI (available commercially from Varian Medical Systems, Palo Alto, Calif.), though a host of other commercial options exist including many from Varian.

As used herein, "coded aperture" refers to an element that is capable of functioning in the fashion described herein. Coded apertures can be described as essentially patterned opaque elements, wherein each code feature modulates x-rays independent of the angle at which the x-rays are incident on the feature. Coded apertures can also be referred to by alternative names, such as masks, encoders, and modulators. A variety of materials can be used to form a coded aperture, including but not limited to, copper, lead, brass, tungsten, gold, silver, bismuth, tin, vanadium, gallium, and others. Coded apertures can have thicknesses on the order of 0.1-10.0 mm and feature sizes on the order of 0.1-10.0 mm. Coded apertures can have any number of features.

The first coded aperture 112 is positioned to receive the x-ray energy. In use, the first coded aperture 112 produces at least two coded x-ray beams from the x-ray energy. The distance between the x-ray source 110 and the first coded aperture 112, referred to in some cases herein as the source-first-coded-aperture distance, can be between 5 mm and 1000 mm. The first coded aperture 112 is configured to provide a first unique code to each of the at least two coded x-ray beams. In use, the first coded aperture 112 modulates the x-ray energy and controls which part of the sample is illuminated as a function of space and time.

The at least two coded x-ray beams can be at least three, at least four, at least five, at least ten, at least fifty, at least one hundred, or more coded x-ray beams. The at least two coded x-ray beams can be pencil beams, fan beams, cone beams, or any combination thereof. In some cases, the at least two coded x-ray beams are at least two coded pencil x-ray beams.

The sample mount 114 includes a sample location that is positioned to allow the at least two coded x-ray beams to pass through the sample location. The sample mount 114 is configured to retain a sample (e.g., tissue samples 116) at the sample location. A person having ordinary skill in the spectroscopic arts would appreciate the wide variety of sample mounts 114 that could fill this purpose and the specific implementation of a sample mount 114, so long as it meets the above-referenced specifications, is not intended to be limiting.

The sample mount 114 can be configured to retain a sample (e.g., tissue samples 116) having a thickness of between 0.5 mm and 200.0 mm in the sample location. The sample mount 114 can be configured to retain a sample having an area of between 25 mm$^2$ and 400 cm$^2$ in the sample location.

In some cases, the system 100 can be configured to substantially limit relative motion between the sample location of the sample mount 114 and the at least two coded x-ray beams to motion that is substantially perpendicular to the at least two coded x-ray beams. In some cases, the sample mount 114 can be configured to substantially prevent rotation of the sample.

In some cases, the system 100 can be configured to move the sample location of the sample mount 114 relative to the x-ray source 110, the first coded aperture 112, the second coded aperture 120, and/or the x-ray detector array 122.

The sample mount 114 can include a sample translation system, such as a mount translation stage optionally coupled to one or more motors, to move the sample mount relative to the other parts of the system. This affords the ability to raster scan the sample to provide an image of a larger area of the sample. The processor 104 can be in electronic communication with the mount motor and can be configured to control the mount motor.

In some cases, the system 100 can be configured to move the x-ray source 110, the first coded aperture 112, the second coded aperture 120, and the x-ray detector array 122 relative to the sample location of the sample mount 114. The system 100 can include a system translation stage configured to move these parts of the system 100. The system 100 can include a system motor coupled to the system translation stage and configured to move these parts of the system 100. The processor 104 can be in electronic communication with the system motor and can be configured to control the system motor.

Relative motion of the sample can be highly precise, with spatial resolution of between 10 μm and 1000 μm. Relative motion can be in three-dimensions and can include rotation of the sample relative to the rest of the system 100.

The second coded aperture 120 is positioned to receive the at least two coded x-ray beams. In use, the second coded aperture 120 isolates transmission signals and scatter signals 118 from each of the at least two coded x-ray beams. The second coded aperture 120 can be configured to provide a second unique code to each of the plurality of second coded aperture pixels within the second coded aperture 120. In use, the second coded aperture 120 demodulates the scatter signal and controls which x-ray detector pixels are illuminated as a function of space and time.

The x-ray detector array 122 includes a plurality of x-ray detector pixels. The plurality of x-ray detector pixels are positioned to receive the transmission signals and the scatter signals 118. The x-ray detector array 122 can be a one-dimensional array of the x-ray detector pixels. The x-ray detector array 122 can be a two-dimensional array of the x-ray detector pixels. The x-ray detector array 122 can include any number of x-ray detector pixels, including but not limited to between 10 x-ray detector pixels and 100,000,000 x-ray detector pixels, between 100 x-ray detector pixels and 10,000,000 x-ray detector pixels, or between 1000 x-ray detector pixels and 25,000 x-ray detector pixels. The x-ray detector array 122 can have a spatial resolution of between 10 μm and 1000 μm.

The plurality of x-ray detector pixels can be energy-sensitive. Each of the plurality of x-ray detector pixels can have an energy resolution of between 1 keV and 150 keV full-width at half maximum (FWHM), including but not limited to, an energy resolution of between 1 keV and 10 keV FWHM or between 5 keV and 50 keV FWHM. The plurality of x-ray detector pixels can in some cases have a pixel pitch of between 0.05 mm and 1.0 mm. The plurality of x-ray detector pixels can be made of cesium iodide, cadmium-zinc-telluride, cadmium telluride, silicon photodiodes, and others understood by those having ordinary skill in the art to be useful for detecting the x-rays described herein. Commercially available arrays or pixels include, but are not limited to, MultiX ME-100 version 2, Varex PaxScan 3024 series, Teledyne Dalsa Xineos series, and the like. The resolution limit of 150 keV FWHM includes detectors that do not provide energy sensitivity.

The processor 104 is in direct or indirect electronic communication with the x-ray source 110, the first coded aperture 112, the second coded aperture 120, and the x-ray detector array 122.

The memory has stored thereon a tissue identification algorithm and instructions that, when executed by the processor 104, cause the processor 104 to: direct the x-ray source 110 to emit the x-ray energy; direct the first coded aperture 112 to produce the at least two coded x-ray beams from the x-ray energy; record a relative position of the sample location; direct the second coded aperture 120 and the x-ray detector array 122 to acquire transmission data and diffraction data for each of the at least two coded x-ray beams; determine one or more properties of a tissue sample 116 positioned within the sample location of the sample mount 114 using the tissue identification algorithm and the transmission data and/or the diffraction data; and generate a report (e.g., as shown via the user interface 108) including the relative position of the sample location and the one or more properties of the tissue sample 116. In some cases, the instructions, when executed by the processor 104, cause the processor 104 to direct the sample mount movement system to move the sample mount 114 to a desired location.

The tissue identification algorithm can optionally operate without identifying a tissue type prior to generating the report. In other words, the algorithm is not necessarily informed of the general category of tissue that is being scanned prior to processing the data. The tissue identification algorithm can include a machine-learning-based classification system that is trained on raw, non-reconstructed data. In some cases, the tissue identification algorithm does not reconstruct raw data prior to making a determination of the likelihood of cancer. The tissue identification algorithm uses a correlation-based classifier to compare measured signals and/or reconstructed images to a library of known signals and/or images, identify a closest match, and determine cancer likelihood based on the matched tissue's class label.

The system 100 can optionally include one or more source-side collimators 111. The one or more source-side collimators 111 can be configured to receive the x-ray energy from the x-ray source 110 and collimate the x-ray energy prior to its arrival at the first coded aperture 112. The one or more source-side collimators 111 can be configured to work in concert with the first coded aperture 112 to collimate the at least two coded x-ray beams. The source-side collimator 111 may consist of a thick element with angled features, or a multitude of one or more thin elements with some finite distance between them. The collimator or collimators would contain specific features depending on the desired beam shape, for example a single hole for a pencil beam, a slit for a fan beam, or a specific hole pattern for a structured beam.

The coded apertures described herein can themselves function as collimators.

The system 100 can also include one or more detector-side collimators. In some cases, the second coded aperture 120 functions as the detector-side collimator. In certain cases, the terms coded aperture and collimator can be used interchangeably.

The system 100 can optionally include the display 106. The display can be in electronic communication with the processor 104 and can be configured to show experimental results acquired by the system.

The system 100 can include a computer with a processor and/or a CPU and a memory.

The processor and/or CPU can be configured to read and perform computer-executable instructions stored in the memory. The computer-executable instructions can include all or portions of the methods described herein.

The memory can include one or more computer readable and/or writable media, and may include, for example, a magnetic disc (e.g., a hard disk), an optical disc (e.g., a DVD, a Blu-ray, a CD), a magneto-optical disk, semiconductor memory (e.g., a non-volatile memory card, flash memory, a solid state drive, SRAM, DRAM), an EPROM, an EEPROM, and the like. The memory can store the computer-executable instructions for all or portions of the methods described herein.

Methods

Figure 3:
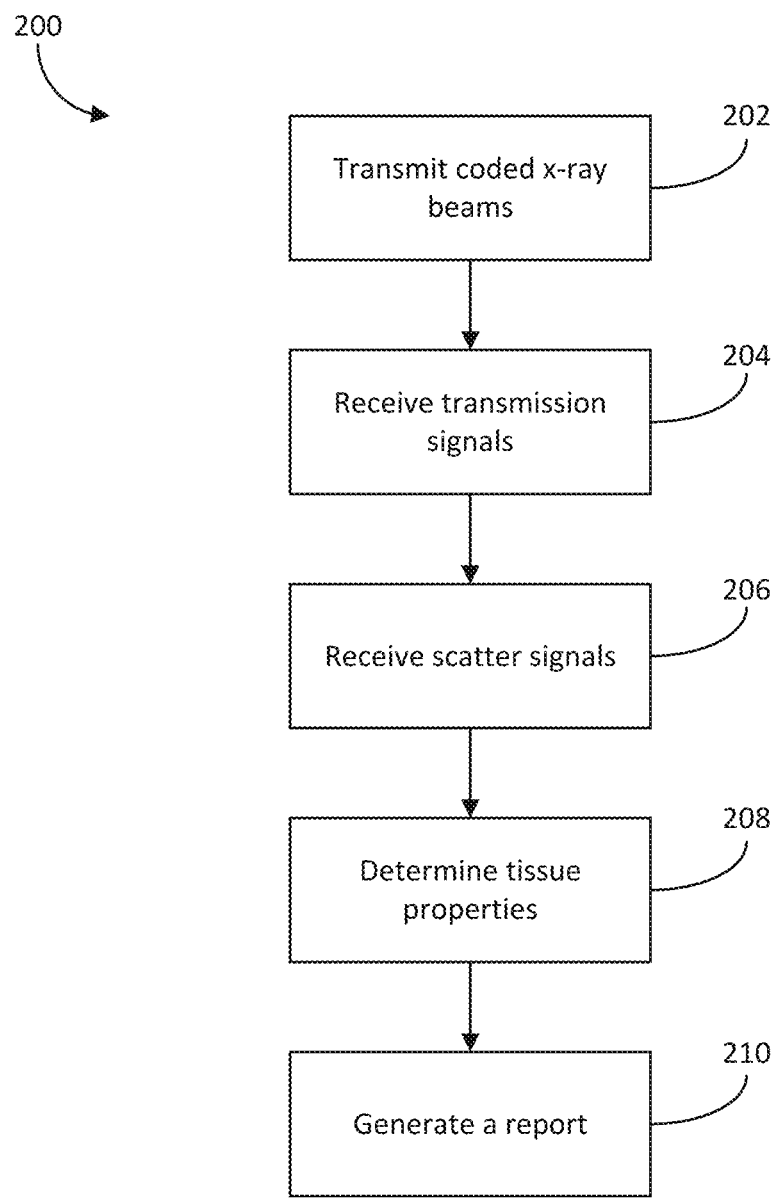
FIG. 3 is a process diagram of a method in accordance with aspects of the present disclosure.

This disclosure provides a method. FIG. 3 shows a process 200 in accordance with methods of the present disclosure. The process 200 includes, at process block 202, transmitting coded x-ray beams. In some implementations, this can include transmitting at least two coded x-ray beams from a coded x-ray source into a sample. The process 200 further includes, at process block 204, receiving transmission signals. In some implementations, this can include receiving transmission signals corresponding to each of the at least two coded x-ray beams. Additionally, the process 200 includes, at process block 206, receiving scatter signals. In some implementations, this can include receiving scatter signals corresponding to each of the at least two coded x-ray beams. As shown, the process includes, at process block 208, determining tissue properties. In some implementations, this can include determining (using a computer-executed tissue identification algorithm), one or more tissue properties based on the transmission signals and/or the scatter signals. The process 200 further includes, at process block 210, generating a report. In some implementations, this can include generating a report including the one or more tissue properties. The process 200 can, in some implementations, include additional steps and/or sub-steps.

The features of the systems described elsewhere herein are applicable to the methods described herein, unless otherwise expressly indicated.

The x-rays utilized in these methods can have the properties outlined herein. The at least two coded x-ray beams can each have a size that would be understood by a person having ordinary skill in the art to be useful for a given application, including but not limited to a diameter of between 0.1 mm and 10.0 mm or between 1.0 mm and 5.0 mm. The at least two coded x-ray beams can be uniform or can have non-uniformity that is compensated in post-processing using methods understood by those having ordinary skill in the x-ray arts. The at least two coded x-ray beams can be provided in a variety of geometries relative to one another and the specific geometry of the beams is not intended to be limiting.

The one or more tissue properties can include a likelihood of cancer.

In some cases, the receiving of process block 204 and the receiving of process block 206 happen simultaneously. In some cases, the sample is not rotated during process blocks 202, 204, 206.

In some cases, the method further comprises moving the sample to a different position and repeating the steps of the method. This process can be repeated numerous times at numerous locations in order to provide a scan of a large area sample. The sample can be moved as described below, including automated movement of the sample. In some cases, the sample can be raster scanned. In implementations involving a fan beam geometry, the sample can be scanned in a single direction. In implementations involving a cone beam geometry, scanning may not be required.

The sample can have size dimensions discussed below with respect to the sample mount. The sample can be any tissue of pathological interest. The sample can be human tissue. The sample can be a pathological specimen involving cancer and other diseases and/or anomalies in the breast, colon, rectum, colorectal, lung, liver, prostate, bone, brain, and other organs. The specific sample is not intended to be limiting to the scope of the disclosure.

The report can take any form, including raw data, processed data, graphical representations of data, images, and the like. In some cases, the report can be an image having a probability of cancer for a given location in the image (e.g., as shown in FIG. 2).

EXAMPLES

Figure 4:
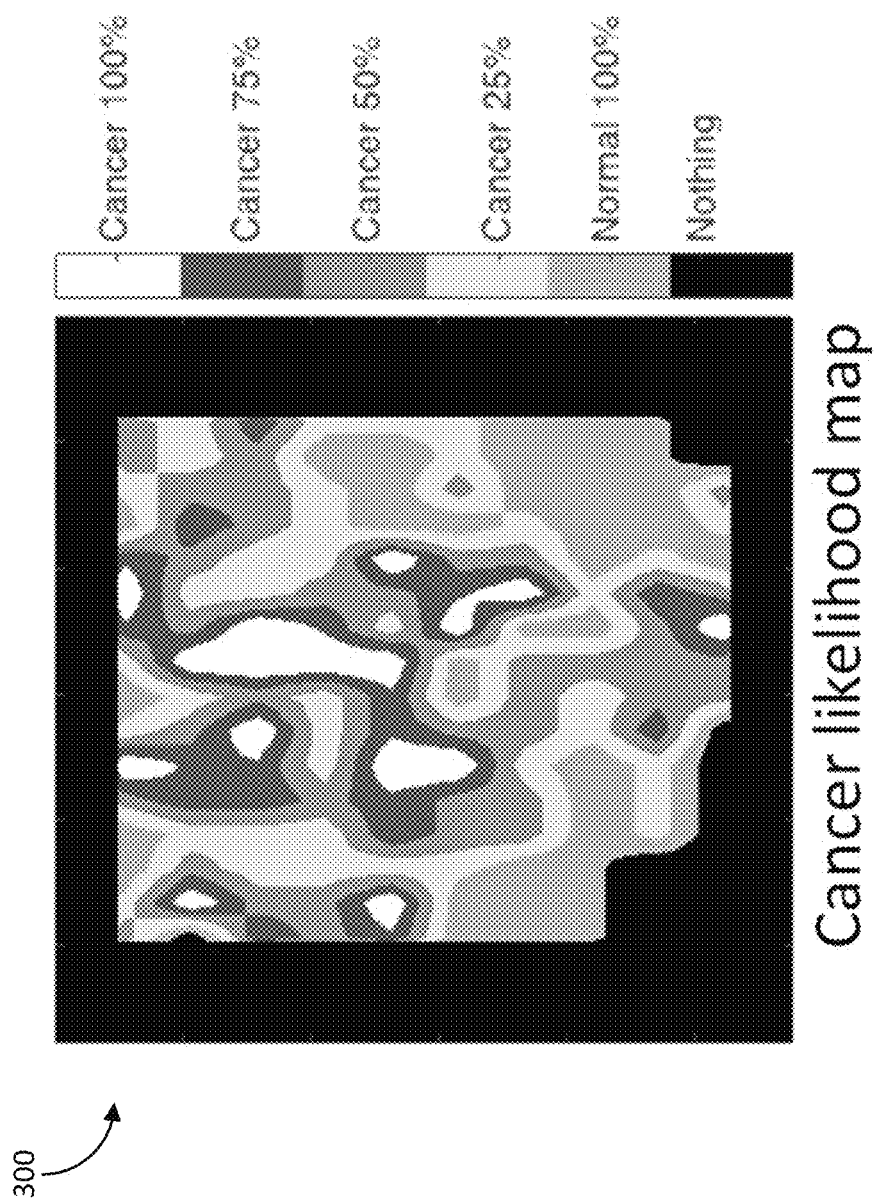
FIG. 4 is an example image of a cancer likelihood map in accordance with aspects of the present disclosure.

The systems and methods described herein were simulated to identify four known materials. Further, the systems and methods described herein were simulated to identify probability of cancer in slices of tissue including at least some cancerous tumors. FIG. 4 is an example output of the system 100. As shown, a map 300 can provide a visual cancer likelihood corresponding to a tissue. As described herein, x-ray diffraction imaging can create the map 300, providing cancer likelihood throughout 100% of the tissue (as an example). Accordingly, the present systems and methods can advantageously provide improved cancer detection accuracy, as well as increased pathology throughput.

In an example implementation of the present disclosure, multiple thin pathology samples were quickly scanned. Analysis was performed via a "checker board" grid of pencil beams and associated coded apertures. A 1 mm pencil beam was used, with scans separated by 5 mm (i.e., ~9-25 scans were needed to fully capture the tissue characteristics). Additionally, a 40 keV source was utilized.

Figures 5A, 5B:
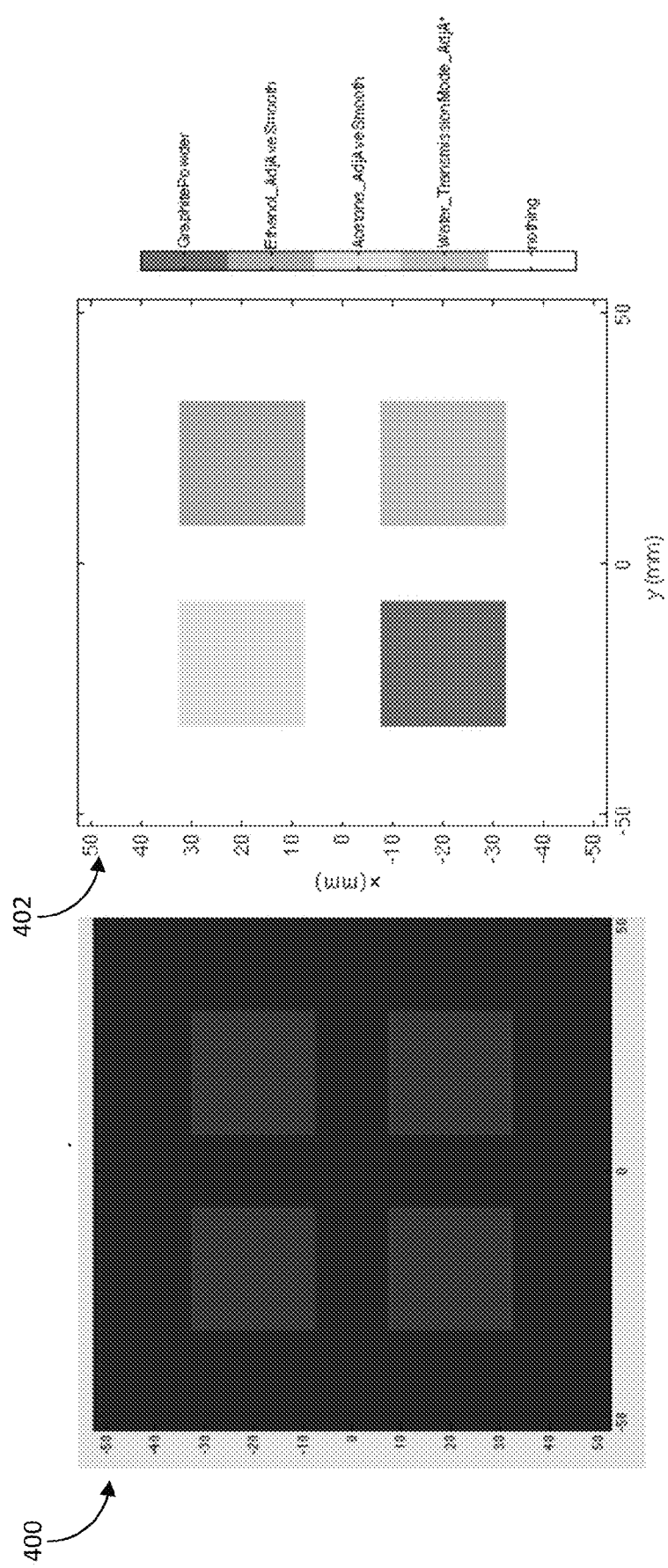
FIG. 5A is an example plot of scatter intensity in accordance with aspects of the present disclosure.
FIG. 5B is an example plot of material composition in accordance with aspects of the present disclosure.
Figure 6:
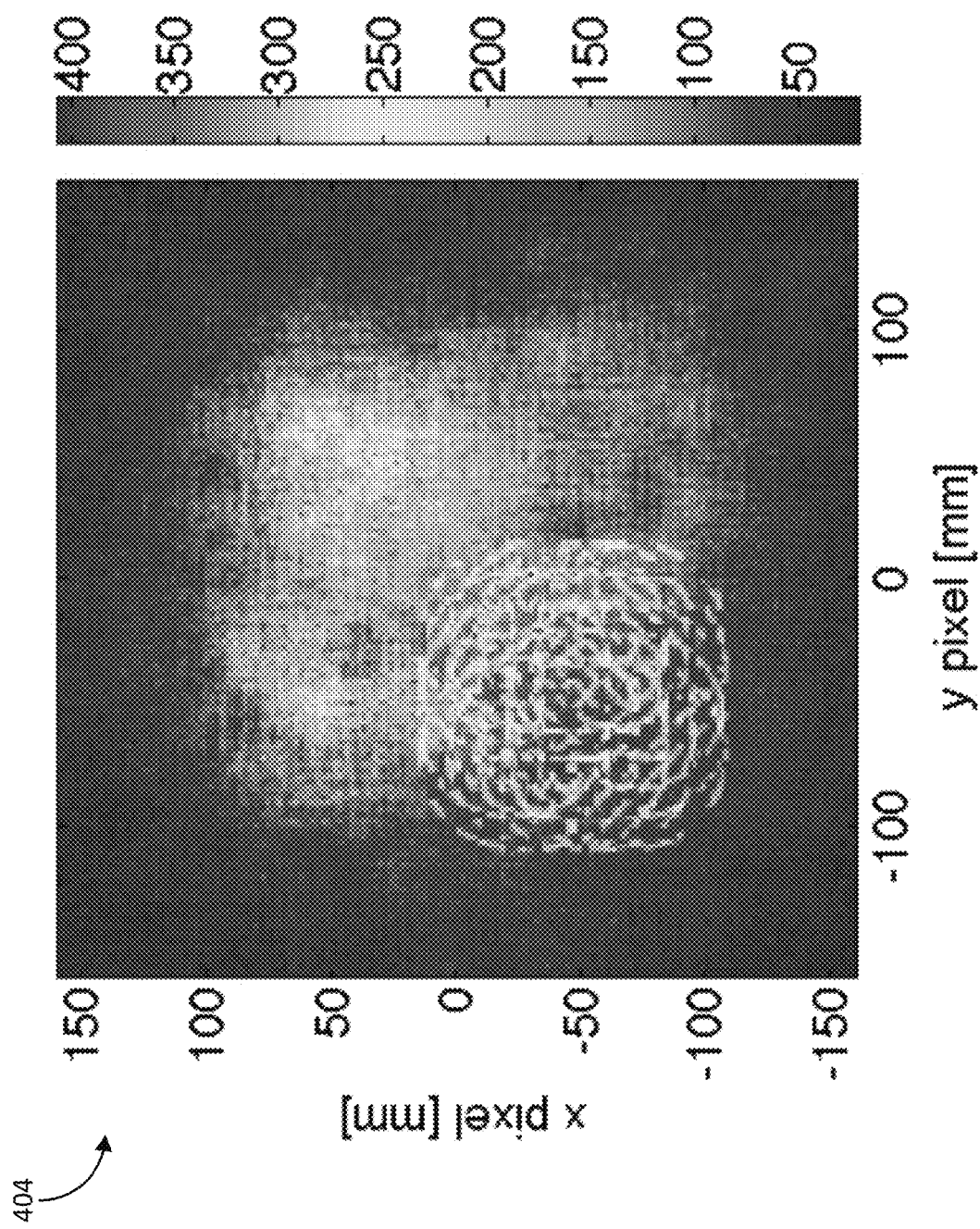
FIG. 6 is an example plot of raw system data in accordance with aspects of the present disclosure.
Figure 7:
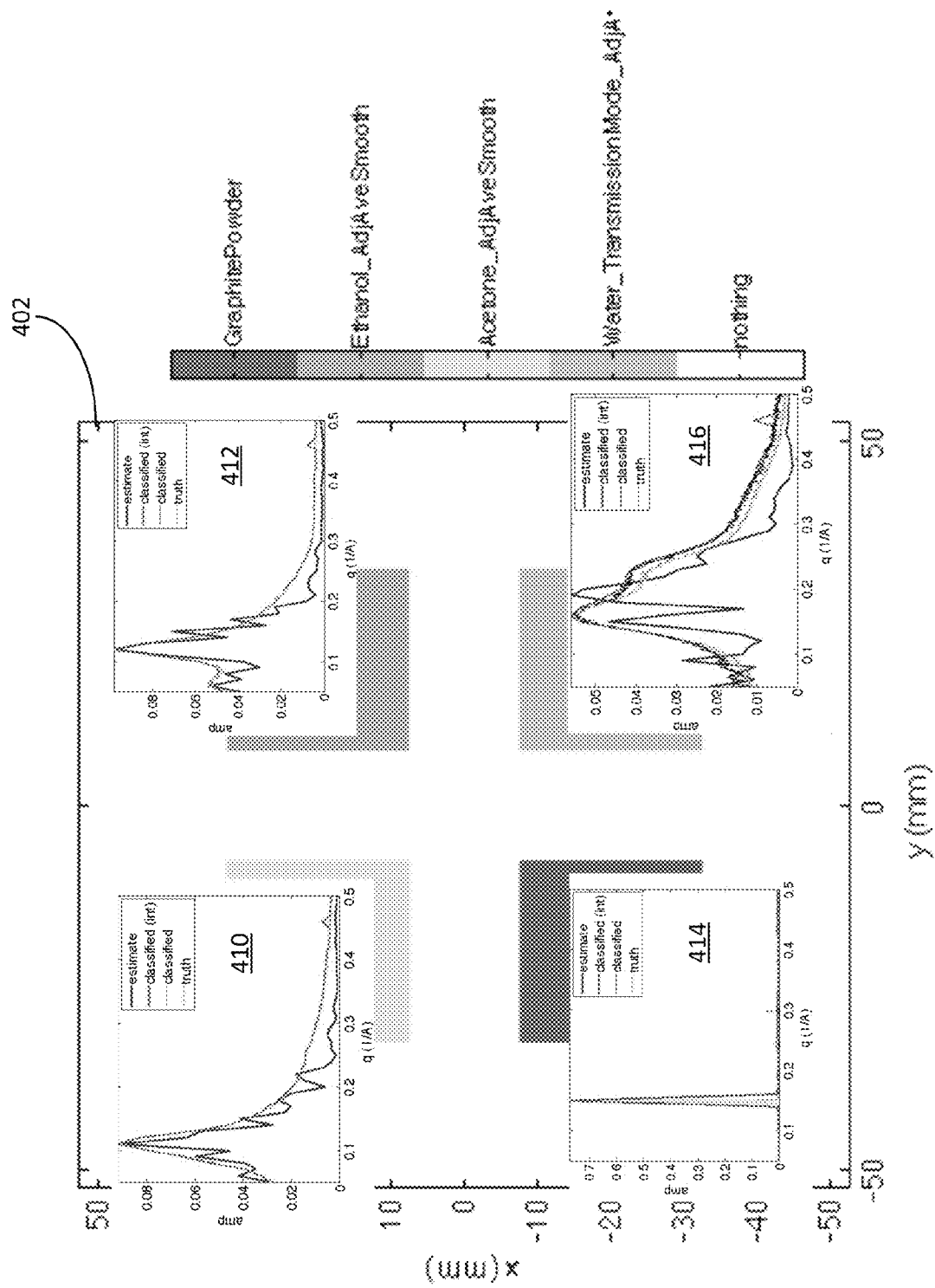
FIG. 7 is an example plot of estimated spectra in accordance with aspects of the present disclosure.

FIG. 5A shows a plot 400 of scatter intensity, and FIG. 5B shows a plot 402 of material composition. The raw simulated data (i.e., data with noise) is shown via plot 404 in FIG. 6. As previously mentioned, the energy source used produced 40 keV. Referring to FIG. 7, the plot 402 is shown with the estimated spectra and resulting classifications.

The systems and methods described herein were also simulated to identify probability of cancer in slices of tissue including at least some cancerous tumors. The simulation process and results are shown via FIGS. 8A-14E.

Figure 8A:
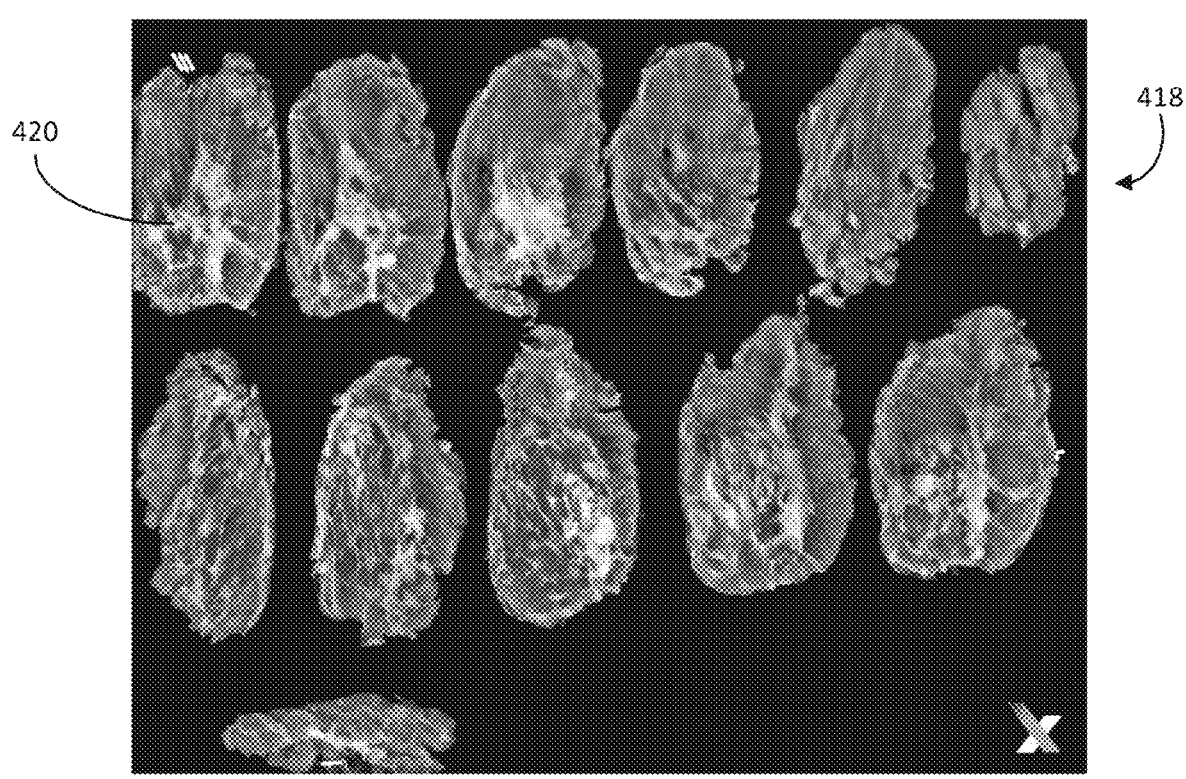
FIG. 8A is a full resolution image of tumor slices in accordance with aspects of the present disclosure.
Figure 8B:
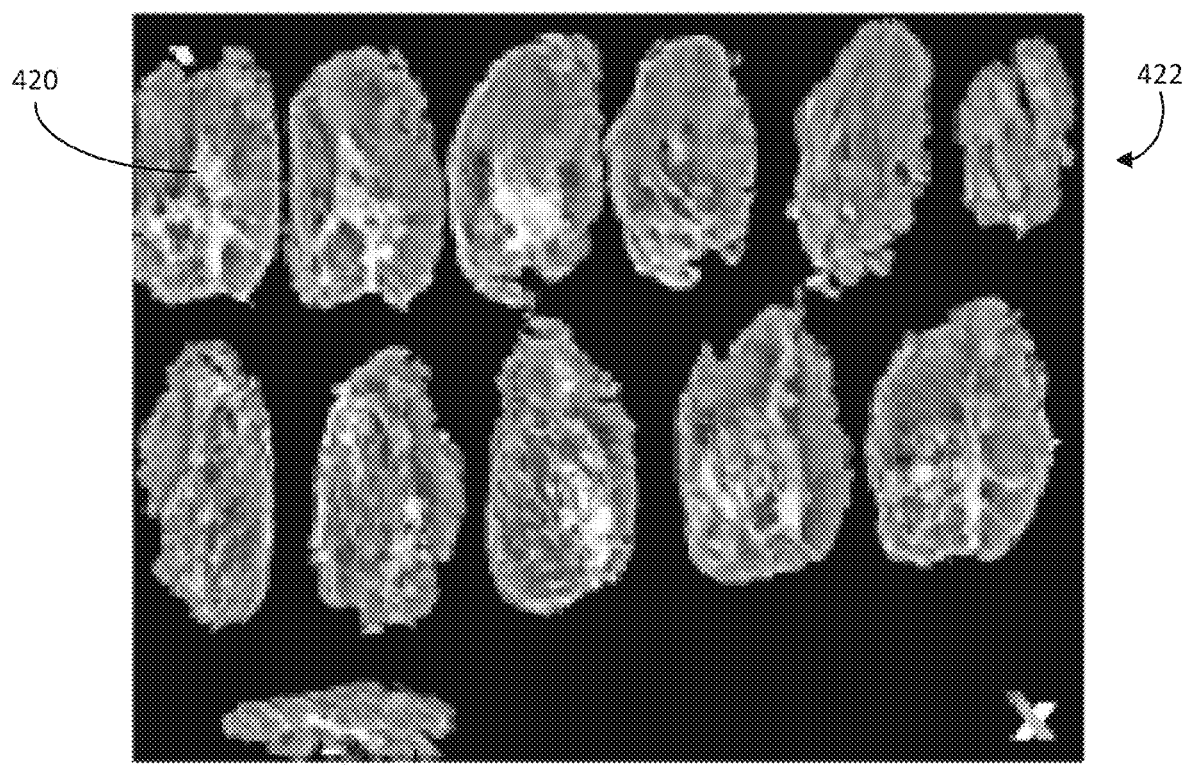
FIG. 8B is a down-sampled image of the tumor slices of FIG. 8A, in accordance with aspects of the present disclosure.
Figure 8C:
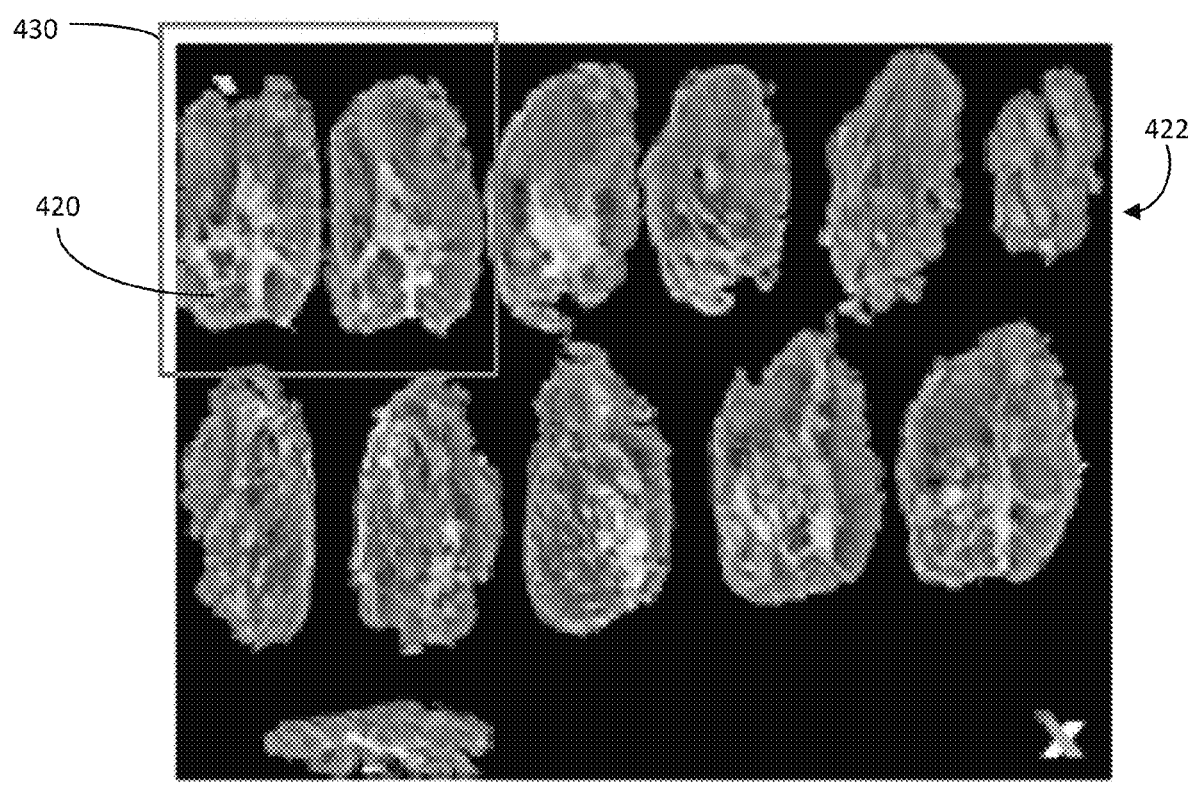
FIG. 8C is an image corresponding to the tumor slices of FIG. 8B, and having a selected region, in accordance with aspects of the present disclosure.
Figure 8D:
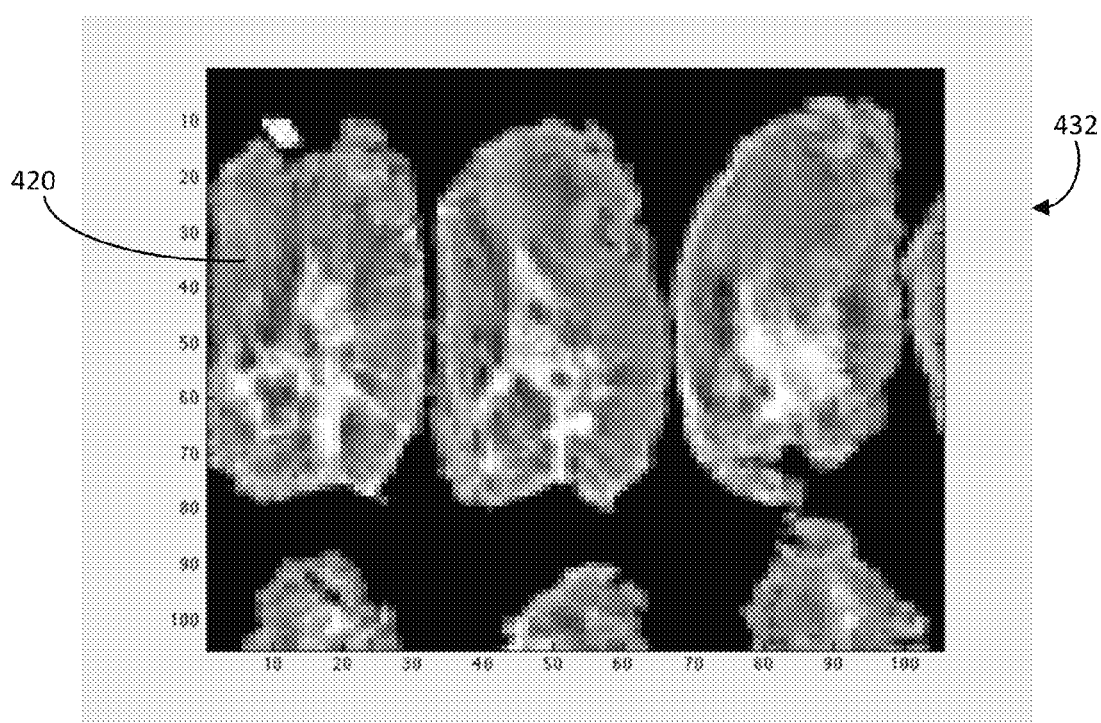
FIG. 8D is a plot of the selected region of FIG. 8C, in accordance with aspects of the present disclosure.

Referring to FIGS. 8A-8D, phantom of tumor slices are shown and manipulated in accordance with aspects of the present disclosure. FIG. 8A is a full resolution image 418 of various slices of a tumor 420. FIG. 8B is a down-sampled image 422 of the various slices of the tumor 420. The presently described simulation down-sampled the full resolution image 418 to 200×200 (i.e., 20×20 cm in 1 mm steps). FIG. 8C again shows the down-sampled image 422, including the slices of the tumor 420. As shown, a selection region 430 (here, a 10×10 cm region) includes a portion of the down-sampled image 422. FIG. 8D is a plot 432 of the selected region 430.

Figure 9:
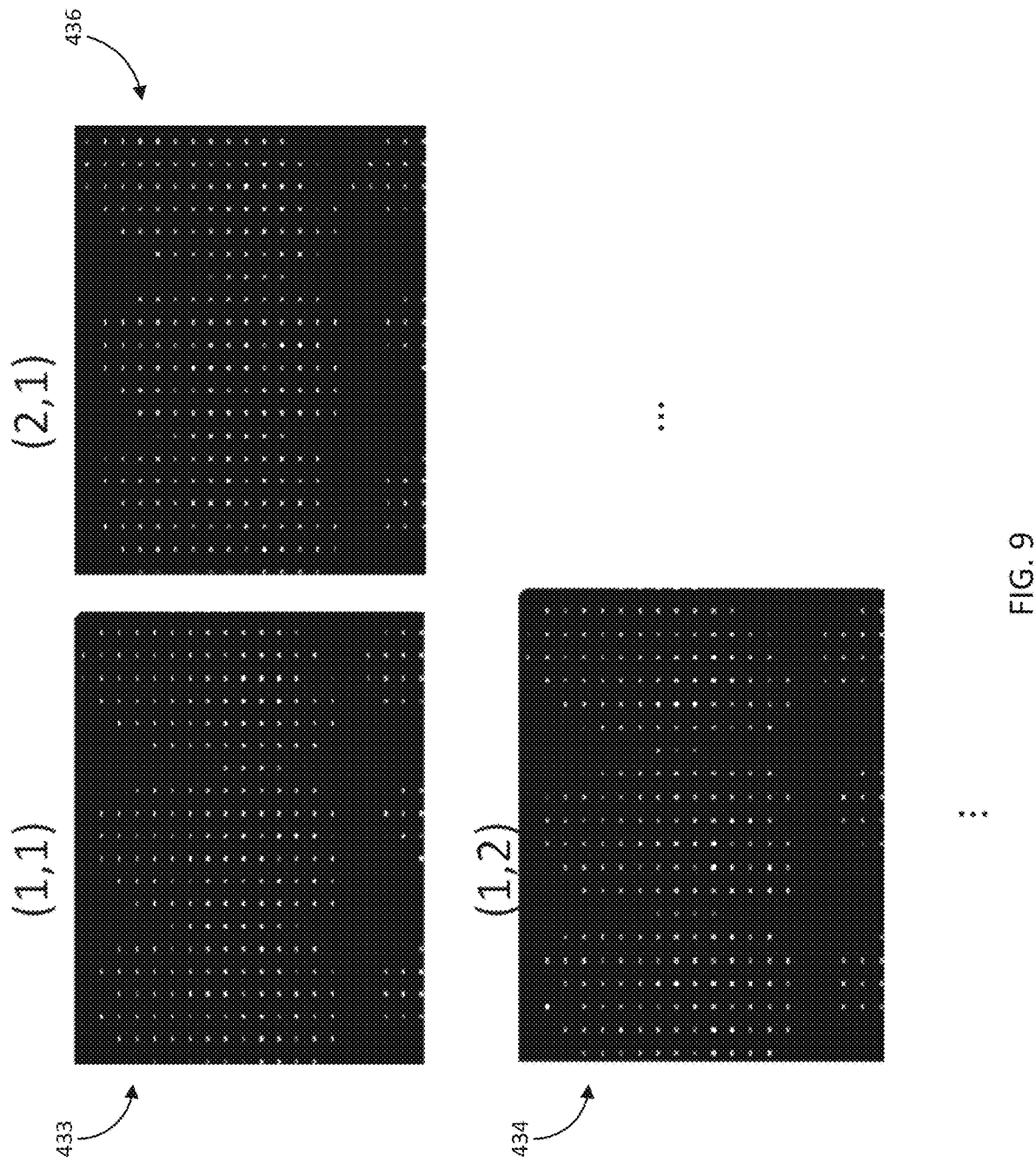
FIG. 9 is an array of image sub-regions corresponding to FIG. 8D, in accordance with aspects of the present disclosure.

Referring now to FIG. 9, the plot 432 of the selected region 430 was split into 25 different sub-regions (e.g., corresponding to the sections of the tissue images in a single acquisition using the checkerboard approach). Three example sub-regions (433, 434, 436) of the array of 25 sub-regions are shown via FIG. 9.

Figures 10A, 10B:
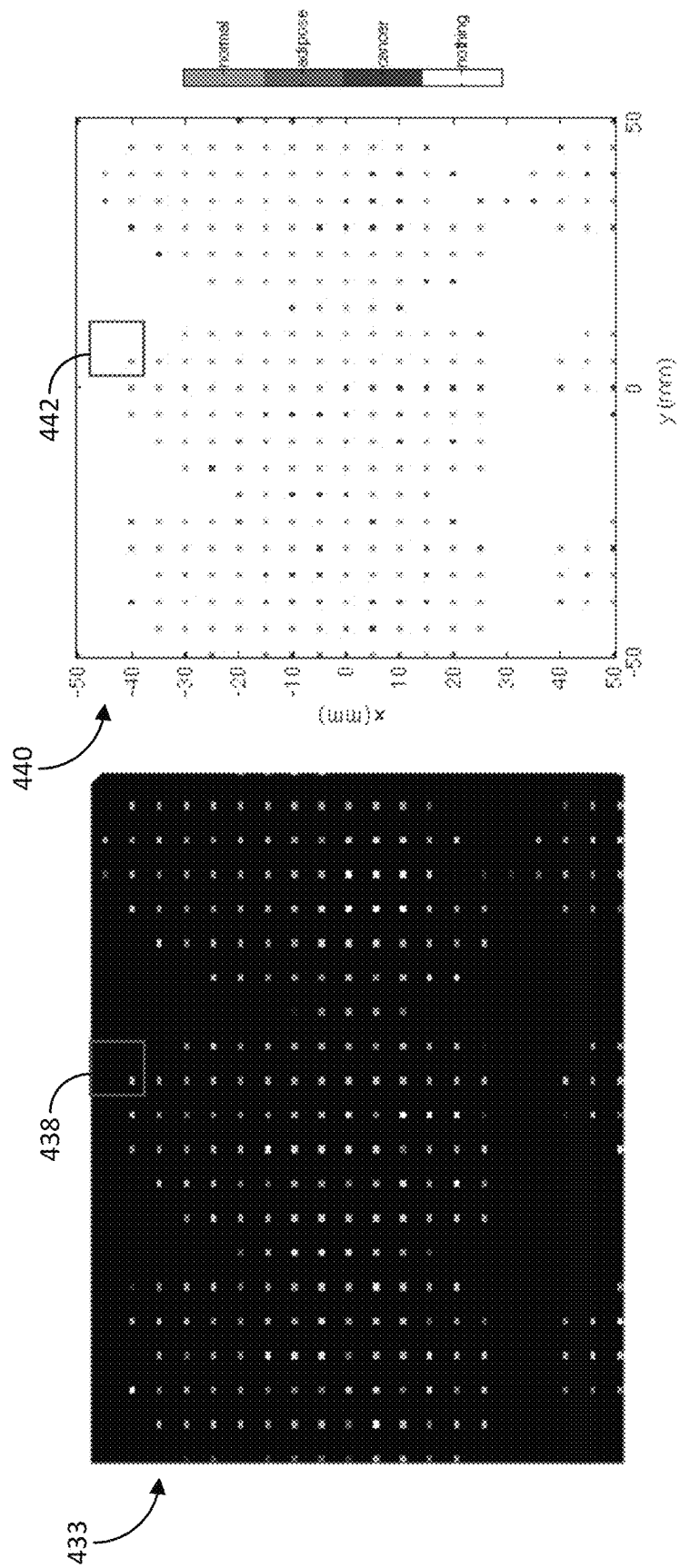
FIG. 10A is one of the image sub-regions from the array of FIG. 9, in accordance with aspects of the present disclosure.
FIG. 10B is a plot of pixel properties corresponding to the image of FIG. 10A, in accordance with the present disclosure.

Referring to FIGS. 10A-10B, individual pixel analysis and classification is shown. FIG. 10A shown one sub-region 433 in detail. Notably, each sub-region includes a plurality of pixels corresponding to various portions of the tissue. For the sake of discussion, one pixel 438 is specifically identified. FIG. 10B is a plot 440 of the sub-region 433, with each pixel assigned to a material property based on pixel value in the transmission image. Each pixel within plot 440 is classified as "normal," "adipose," "cancer," or "nothing." The pixel 438, for example, is transformed to indicate "normal" tissue, as shown by plotted pixel 442. As shown, all scatter intensities were normalized to 1.

Figure 11:
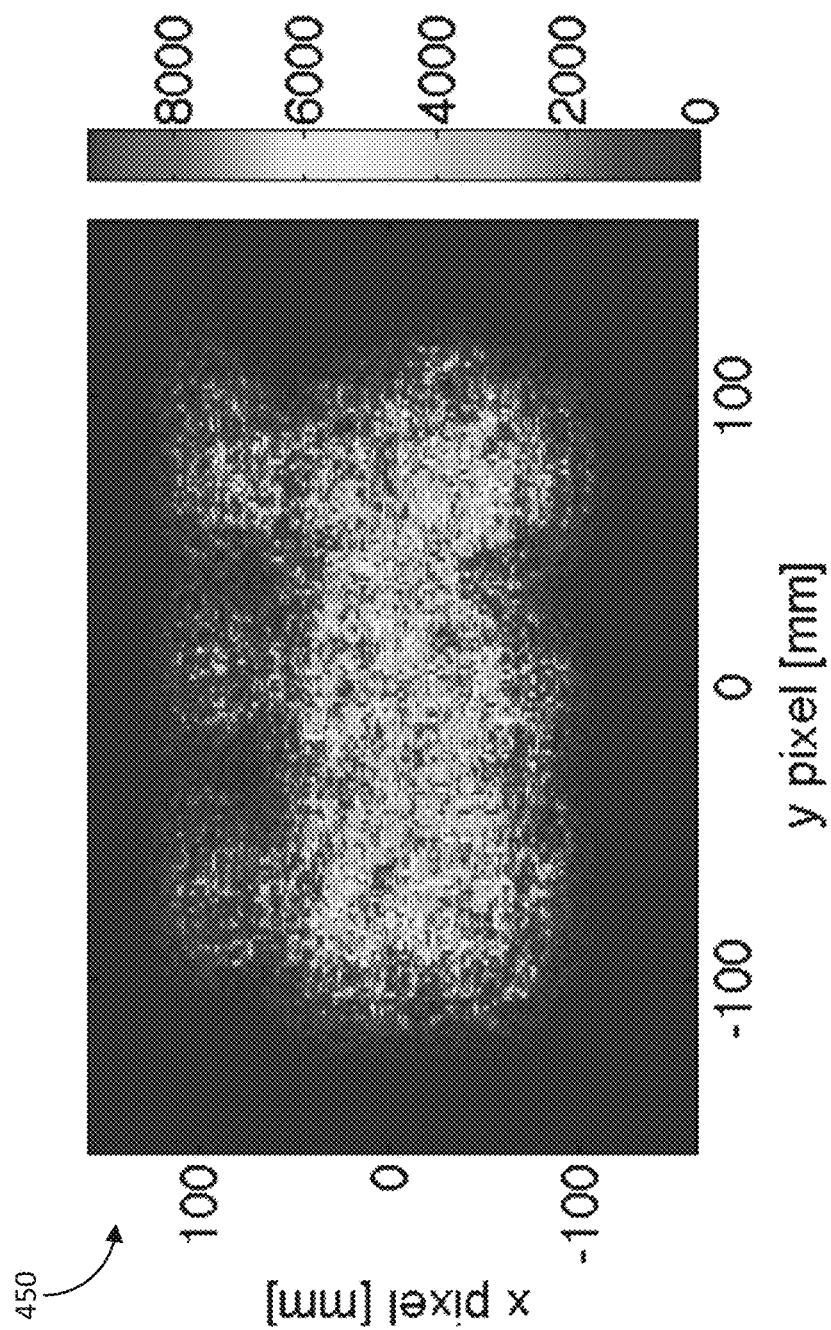
FIG. 11 is a plot of simulated data, in accordance with the present disclosure.

FIG. 11 is a plot 450 of generated simulation data, according to aspects of the present disclosure. The particular generated data was produced at 60 keV using 7 degree acceptance collimation at the detector.

Figures 12A, 12B:
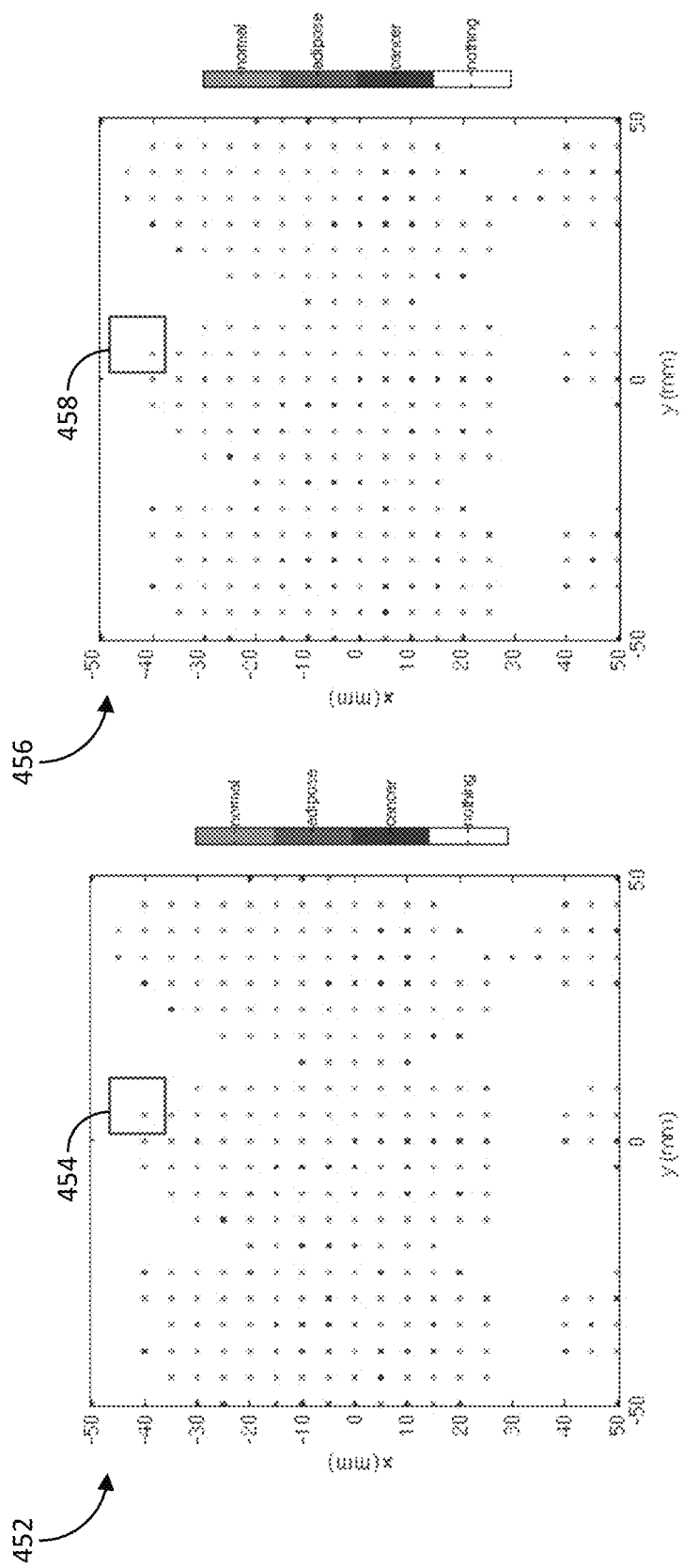
FIG. 12A is a plot of classified reconstructed data, in accordance with the present disclosure.
FIG. 12B is a plot of ground truth data corresponding to the reconstructed data of FIG. 12A, in accordance with the present disclosure.

Referring now to FIGS. 12A-12B, a comparison between a classified reconstruction (FIG. 12A) and ground truth (FIG. 12B) is provided. As shown, a plot 452 includes a plurality of classified pixels (e.g., pixel 454) resulting from the simulation. Notably the simulation plot 452 is substantially similar to the ground truth plot 456. As shown, pixel 454 is correctly classified, when compared to corresponding pixel 458. Next, the tissue can be moved in 1 mm increments along the transverse directions to ensure that the entire tissue is sampled.

Figures 13A, 13B:
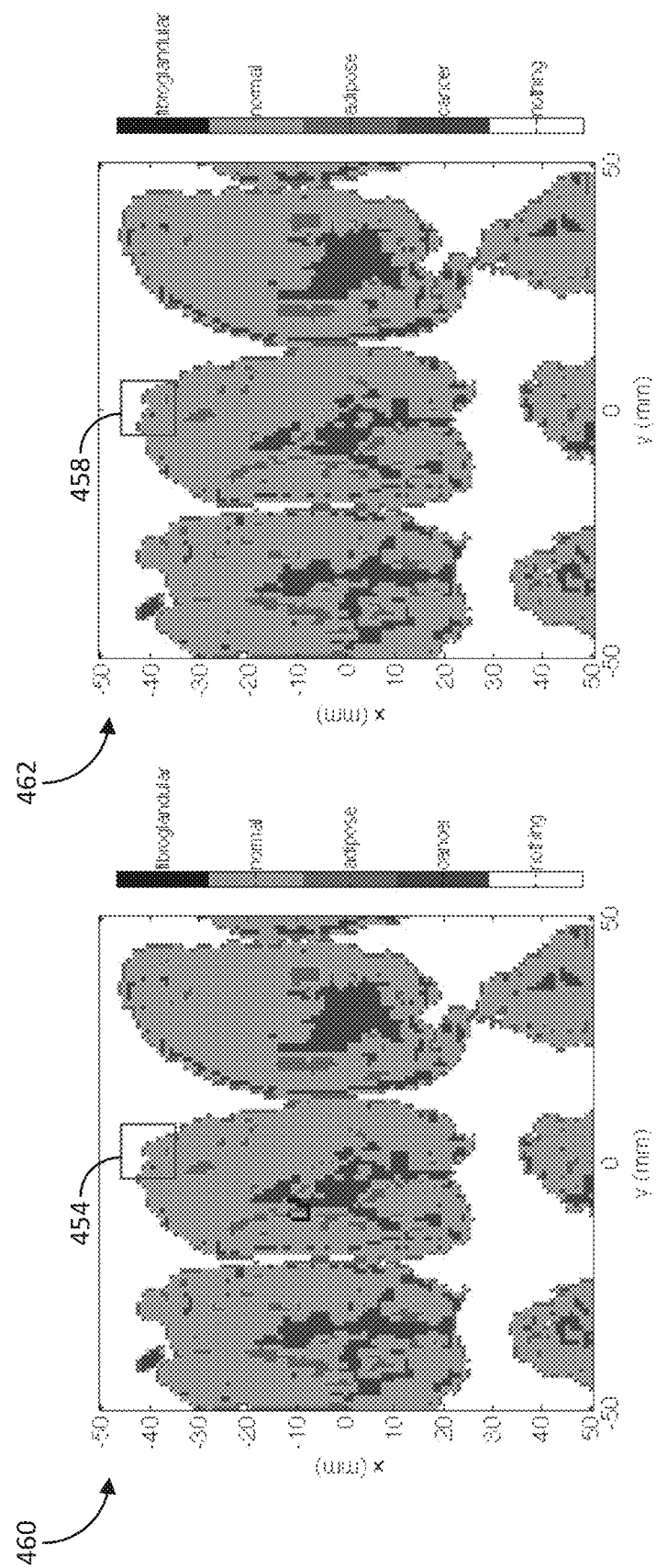
FIG. 13A is a plot of reconstructed data, in accordance with the present disclosure.
FIG. 13B is a plot of ground truth data corresponding to the reconstructed data of FIG. 13A, in accordance with the present disclosure.

Referring now to FIGS. 13A-13B, the classified scans can be "stacked" together to form a reconstructed image of the full tissue slice. FIG. 13A is a plot 460 of the reconstructed tissue slice, classified by tissue type. Stacking/stitching the scans back together provides a map of the tissue type at each location. Notably, the simulation plot 460 is substantially similar to the ground truth plot 462.

FIGS. 14A-14D provide two additional simulation plots and their corresponding ground truth plots. FIG. 14A is a plot 461 of the reconstructed tissue slice. Here, the plot 461 is an image showing a simple binary classification of cancer or non-cancerous tissue. Again, the simulation plot 461 is substantially similar to the ground truth plot 463.

FIG. 14C is a plot 464 of a reconstructed cancer score (here, log(correlation between recovered spectrum and cancer)). Notably, the plot 464 provides valuable data that is not otherwise apparent from the ground truth transmission image, shown via the plot 432 of FIG. 14D. The plot 464 shows how likely each pixel is to be cancer. Accordingly, this can be used by a technician and/or the physician to choose which tissue slices to analyze via microscopy.

Figure 14E:
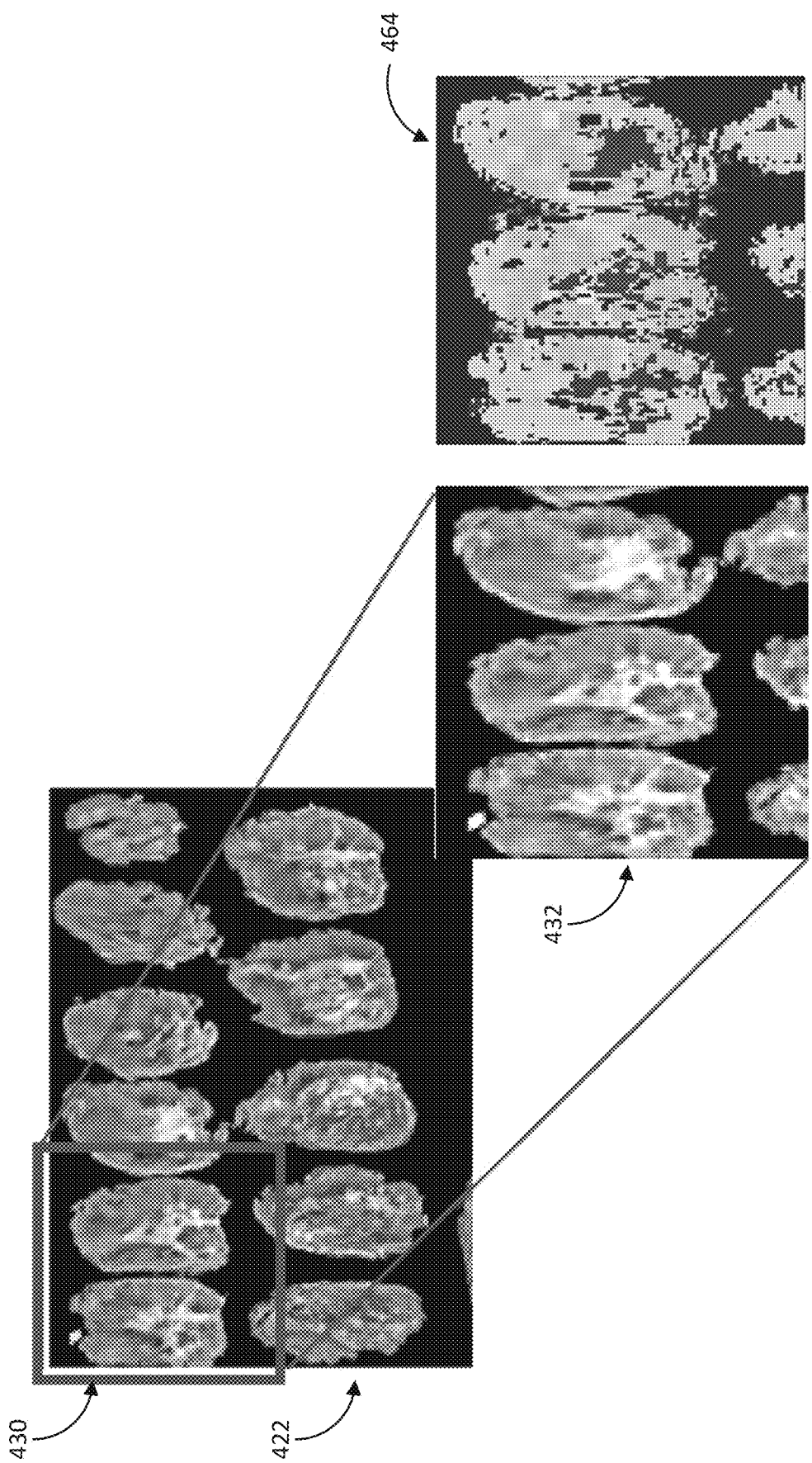
FIG. 14E is an example of system input and output images, in accordance with the present disclosure.

FIG. 14E is a comparison of the input and output of the simulation (i.e., example inputs and outputs corresponding to the systems and methods described herein). The selected region 430 of the down-sampled image 422 provides plot 432. The plot 464 provides a corresponding reconstructed cancer score for use in diagnosis and treatment.

We claim:

1. A system comprising:
   an x-ray source that, in use, produces an x-ray energy;
   a first coded aperture positioned to receive the x-ray energy, the first coded aperture, in use, produces at least two coded x-ray beams from the x-ray energy;
   a sample mount having a sample location positioned to allow the at least two coded x-ray beams to pass through the sample location, the sample mount configured to retain a sample at the sample location;
   a second coded aperture positioned to receive the at least two coded x-ray beams, the second coded aperture, in use, isolates transmission signals and scatter signals from each of the at least two coded x-ray beams;
   an x-ray detector array comprising a plurality of x-ray detector pixels, the plurality of x-ray detector pixels positioned to receive the transmission signals and the scatter signals;
   a processor in direct or indirect electronic communication with the x-ray source, the first coded aperture, the second coded aperture, and the x-ray detector array; and
   a memory having stored thereon a tissue identification algorithm and instructions that, when executed by the processor, cause the processor to: direct the x-ray source to emit the x-ray energy; direct the first coded aperture to produce the at least two coded x-ray beams from the x-ray energy; record a relative position of the sample location; direct the second coded aperture and the x-ray detector array to acquire transmission data and diffraction data for each of the at least two coded x-ray beams; determine one or more properties of a tissue sample positioned within the sample location of the sample mount using the tissue identification algorithm and the transmission data and/or the diffraction data; and generate a report including the relative position of the sample location and the one or more properties of the tissue sample.

2. The system of claim 1, further comprising one or more source-side collimators configured to receive the x-ray energy from the x-ray source and collimate the x-ray energy prior to the arrival of the x-ray energy at the first coded aperture.

3. The system of claim 1, further comprising one or more source-side collimators configured to work jointly with the first coded aperture to collimate the at least two coded x-ray beams.

4. The system of claim 1, wherein the first coded aperture is configured to provide a first unique code to each of the at least two coded x-ray beams.

5. The system of claim 1, wherein a relative motion between the sample location of the sample mount and the at least two coded x-ray beams is substantially limited to a motion that is substantially perpendicular to the at least two coded x-ray beams.

6. The system of claim 1, wherein the sample location of the sample mount is configured to move relative to the x-ray source, the first coded aperture, the second coded aperture, and/or the x-ray detector array.

7. The system of claim 6, further comprising a mount translation stage coupled to the sample mount and configured to provide a movement of the sample location.

8. The system of claim 1, wherein the x-ray source, the first coded aperture, the second coded aperture, and the x-ray detector array are configured to move relative to the sample location of the sample mount.

9. The system of claim 8, further comprising a system translation stage coupled to the x-ray source, the first coded aperture, the second coded aperture, and the x-ray detector array, and configured to provide a movement of the x-ray source, the first coded aperture, the second coded aperture, and the x-ray detector array.

10. The system of claim 9, further comprising a system motor coupled to the system translation stage and configured to move the x-ray source, the first coded aperture, the second coded aperture, and the x-ray detector array via the system translation stage.

11. The system of claim 1, wherein the second coded aperture comprises a plurality of second coded aperture pixels, wherein the second coded aperture is configured to provide a second unique code to each of the plurality of second coded aperture pixels within the second coded aperture.

12. The system of claim 1, wherein the tissue identification algorithm comprises a machine-learning-based classification algorithm that is trained on raw, non-reconstructed data.

13. The system of claim 12, wherein the tissue identification algorithm does not reconstruct raw data prior to making a determination of a likelihood of cancer.

14. The system of claim 1, wherein the instructions, when executed by the processor, further cause the processor to generate a transmission image from the transmission signals and a scatter image from the scatter signals.

15. A method comprising:
a) transmitting at least two coded x-ray beams from a coded x-ray source into a sample;
b) receiving transmission signals corresponding to each of the at least two coded x-ray beams;
c) receiving scatter signals corresponding to each of the at least two coded x-ray beams;
d) determining, using a computer-executed tissue identification algorithm, one or more tissue properties based on the transmission signals and/or the scatter signals; and
e) generate a report including the one or more tissue properties.

16. The method of claim 15, wherein the coded x-ray source includes an x-ray source and a coded aperture, and the step a) includes transmitting an x-ray energy from the x-ray source through the coded aperture to generate the at least two coded x-ray beams.

17. The method of claim 15, further comprising moving the sample to a different position and repeating steps a), b), c), d), and e).

18. The method of claim 15, wherein the computer-executed tissue identification algorithm comprises a machine-learning-based classification algorithm that is trained on raw, non-reconstructed data.

19. The method of claim 15, further comprising generating a transmission image from the transmission signals and a scatter image from the scatter signals.

20. The method of claim 19, further comprising overlaying the transmission image and the scatter image.

* * * * *